(12) United States Patent
Newell

(10) Patent No.: US 7,816,319 B2
(45) Date of Patent: Oct. 19, 2010

(54) METHODS AND PRODUCTS FOR MANIPULATING UNCOUPLING PROTEIN EXPRESSION

(75) Inventor: Martha Karen Newell, Colorado Springs, CO (US)

(73) Assignee: University of Vermont and State Agricultural College, Burlington, VT (US)

( * ) Notice: Subject to any disclaimer, the term of this patent is extended or adjusted under 35 U.S.C. 154(b) by 156 days.

(21) Appl. No.: 11/409,446

(22) Filed: Apr. 21, 2006

(65) Prior Publication Data

US 2006/0247199 A1    Nov. 2, 2006

Related U.S. Application Data

(63) Continuation of application No. 09/599,760, filed on Jun. 22, 2000, now abandoned.

(60) Provisional application No. 60/140,574, filed on Jun. 23, 1999.

(51) Int. Cl.
    *A01N 61/00*    (2006.01)
    *A61K 31/00*    (2006.01)
    *C07K 16/00*    (2006.01)
    *C12P 21/08*    (2006.01)

(52) U.S. Cl. ................ 514/4; 514/1; 514/2; 530/387.9; 530/388.8

(58) Field of Classification Search .................... 514/1, 514/2, 44, 4; 530/387.1, 387.9, 388.8
See application file for complete search history.

(56) References Cited

U.S. PATENT DOCUMENTS

| | | |
|---|---|---|
| 4,724,234 A | 2/1988 | Cone, Jr. |
| 4,935,450 A | 6/1990 | Cone, Jr. |
| 5,556,754 A | 9/1996 | Singer et al. |
| 5,585,363 A | 12/1996 | Scanlon et al. |
| 6,113,946 A | 9/2000 | Szoka, Jr. et al. |
| 2003/0150022 A1 | 8/2003 | Newell et al. |
| 2004/0005291 A1 | 1/2004 | Rogers et al. |
| 2005/0042224 A1 | 2/2005 | Newell |
| 2005/0074882 A1 | 4/2005 | Newell |
| 2005/0158333 A1 | 7/2005 | Newell |

FOREIGN PATENT DOCUMENTS

| | | |
|---|---|---|
| WO | WO 98/02579 | 1/1998 |
| WO | WO 98/31396 A1 | 7/1998 |
| WO | WO 98/45313 A1 | 10/1998 |
| WO | WO 98/45438 A1 | 10/1998 |
| WO | PCT/US99/06874 | 3/1999 |
| WO | WO 99/53953 | 10/1999 |
| WO | WO 00/47617 | 8/2000 |
| WO | WO 00/78941 A2 | 12/2000 |
| WO | WO 03/031643 A2 | 4/2003 |

OTHER PUBLICATIONS

Lobato, MN et al., Trends in Molecular Med., vol. 9, No. 9, pp. 390-396 (2003).*
Stayton, PS et al., J. Controlled Release, vol. 65, pp. 203-220 (2000).*
Peracchi, A. et al., Rev. Med. Virol., vol. 14, pp. 47-64 (2004).*
Chirila, T. et al., Biomaterials, vol. 23, pp. 321-342 (2002).*
Agrawal, S. et al., Molecular Med. Today, vol. 6, pp. 72-81 (2000).*
Crooke, S., Annu. Rev. Med., vol. 55, pp. 61-95 (2004).*
Opalinska, J.B., et al., Nature Reviews, vol. 1, pp. 503-514 (2002).*
Branch, A., Trends in Biochem. Sci., vol. 23, pp. 45-50 (1998).*
Agrawal, S. et al. Antisense therapeutics: is it as simple as complementary base recognition? Mol Med Today. Feb. 2000;6(2):72-81. Review. Erratum in: Mol Med Today Mar. 2000;6(3):103.
Arsenijevic, D. et al., "Disruption of the uncoupling protein-2 gene in mice reveals a role in immunity and reactive oxygen species production", *Nature Genetics*, Dec. 2000, pp. 435-439, vol. 26, No. 4.
Asoh, Sadamitsu et al., "Expression of the Apoptosis-Mediator Fas . . . ", J. Biochem., vol. 120, pp. 600-607, 1996.
Babu, P.G. et al., "Genetic Control of Multisystem Autoimmune . . . ", Current Topics in Microbiology and Immunology, vol. 122, pp. 154-161, 1985.
Bach, Jean-Francois, "Insulin-Dependent Diabetes Mellitus as an Autoimmune Disease", Endocrine Society, vol. 15, No. 4, pp. 516-542, Aug. 1994.
Baggetto, LG, "Deviant Energetic Metabolism of Glycolytic Cancer Cells", Biochimie, vol. 74, pp. 959-974, 1992.
Bhushan, A. et al., "Drug Resistance Results in Alterations . . . ", Immunology and Cell Biology 76, pp. 350-356, 1998.
Billingham, Dr. R. E. et al., "Actively Acquired Tolerance' of Foreign Cells", Nature, vol. 172, No. 4379, pp. 603-606, Oct. 3, 1953.
Birnboim, H. Chaim and Jagdeep K. Sandhu, "Levels of DNA Strand Breaks . . . ", Journal of Cellular Biochemistry, vol. 66, pp. 219-228, 1997.
Böhme, J. et al., "Transgenic Mice with I-A on Islet Cells . . . ", Science, vol. 244, pp. 1179-1183, Jun. 9, 1989.

(Continued)

*Primary Examiner*—Jane Zara
(74) *Attorney, Agent, or Firm*—Wolf, Greenfield & Sacks, P.C.

(57) ABSTRACT

The invention is based in part on the discovery that uncoupling proteins (UCPs) are expressed in the plasma membrane of rapidly dividing cells but not of growth arrested, chemotherapy resistant cells. It has also been found according to the invention that UCP is expressed in the lysosomal membrane under certain metabolic conditions. Thus the invention is methods, products, screening assays and kits relating to the manipulation of UCP expression within cellular and intracellular membranes.

4 Claims, No Drawings

OTHER PUBLICATIONS

Bonfoco, Emanuela et al., "Inducible Nonlymphoid Expression of Fas . . . ", Immunity, vol. 9, pp. 711-720, Nov. 1998.

Bouillaud, F. et al. A sequence related to a DNA recognition element is essential for the inhibition by nucleotides of proton transport through the mitochondrial uncoupling protein. EMBO J. Apr 15, 1994;13(8):1990-7.

Branch, A.D. A good antisense molecule is hard to find. Trends Biochem Sci. Feb. 1998;23(2):45-50. Review.

Burrows, F.J. et al. "A murine model for antibody-directed targeting of vascular endothelial cells in solid tumors," Cancer Research, 52(21), Nov. 1, 1992, pg. 5954-62, Abstract.

Caldwell, Kevin K. et al., "Evaluation of Methods for the Isolation . . . ", Analytical Biochemistry, vol. 175, pp. 177-190, 1988.

Cambier, John C. et al., "Ia Binding Ligands and cAMP Stimulate Nuclear Translocation of PKC in B Lymphocytes", Nature, vol. 327, pp. 629-632, Jun. 18, 1987.

Chien, Millie M. et al., "Fas-induced B Cell Apoptosis Requires . . . ", Journal of Biological Chemistry, vol. 274, pp. 1-8, 1999.

Chirila, T.V. et al., The use of synthetic polymers for delivery of therapeutic antisense oligodeoxynucleotides. Biomaterials. Jan. 2002;23(2):321-42. Review.

Chisari, Francis V. et al., "Molecular Pathogenesis of Hepatocellular Carcinoma . . . ", Cell, vol. 59, pp. 1145-1156, Dec. 22, 1989.

Clément, Marie-Véronique and Ivan Stamenkovic, "Superoxide Anion Is A Natural . . . ", EMBO Journal, vol. 15, No. 2, pp. 216-225, 1996.

Conceição-Silva, Fatima et al., "The Resolution of Lesions Induced . . . ", Eur. J. Immunol., vol. 28, pp. 237-245, 1998.

Cosgrove, Dominic et al., "Evaluation of the Functional Equivalence of . . . ", J. Exp. Med., vol. 176, pp. 629-634, Aug. 1992.

Cosgrove, Dominic et al., "Mice Lacking MHC Class II Molecules", Cell, vol. 66, pp. 1051-1066, Sep. 6, 1991.

Cossarizza, Andrea et al., "Mitochondrial Modification During Rat . . . ", Experimental Cell Research, vol. 214, pp. 323-330, 1994.

Craighead, John E. et al., "Diverse Patterns of Immune and Non-Immune . . . ", Journal of Autoimmunity, vol. 3 (Supplement), pp. 27-29, 1990.

Creech, Elizabeth A. et al., "MHC Genes Modify Systemic Autoimmune Disease: The Role of the I-E Locus", Journal of Immunology, vol. 156, pp. 812-817, 1996.

Crooke, S. Antisense Res. and Application. pp. 1-50. (Ed. by S. Crooke) Springer-Verlag, 1999.

Dang, Chi V. And Gregg L. Semenza, "Oncogenic Alterations of Metabolism", TIBS, vol. 24, 1999.

del Carmen Ruiz-Ruiz, María et al., "Activation of Protein Kinase C . . . ", Eur. J. Immunol., vol. 27, pp. 1442-1450, 1997.

Denis-Pouxviel, Colette et al., "Regulation of Mitochondrial Hexokinase in Cultured . . . ", Biochimica et Biophysica Acta, vol. 902, pp. 335-348, 1987.

Desbarats, Julie et al., "Fas (CD95) Expression and Death-Mediating . . . ", Proc. Natl. Acad. Sci. USA, vol. 93, pp. 11014-11018, Oct. 1996.

Desbarats, Julie et al., "Newly Discovered Role for Fas Ligand . . . ", Nature Medicine, vol. 4, No. 12, pp. 1377-1382, Dec. 1998.

Eliopoulos, AG et al. "CD40 Stimulation Augments Apoptosis in Carcinoma Cell Lines," J. Cellular Biochem, (supplemental 19B), Abstract B8-123, pg. 271, 1995.

Fleury, Christophe et al., "Uncoupling Protein-2: A Novel Gene Linked . . . ", Nature Genetics, vol. 15, pp. 269-272, Mar. 1997.

Freedman, M., et al., γδ T-cell-human glial cell interactions . . . susceptibility to cytolysis, J. Neuroimmunology, 74:143-148, 1997.

Fujihashi, Kohtaro et al., "γ/δ T Cell-deficient Mice Have Impaired Mucosal Immunoglobulin A Responses," J. Exp. Med., vol. 183, pp. 1929-1935, Apr. 1996.

Garban, Frédéric et al., "Signal Transduction Via Human Leucocyte . . . ", Experimental Hematology, vol. 26, pp. 874-884, 1998.

Garlid, Kieth D. et al., "The Mechanism of Proton Transport . . . ", FEBS Letters, vol. 438, pp. 10-14, 1998.

Genestier, L., et al., "Caspase-dependent Ceramide Production in Fas- and HLA Class I-mediated Peripheral T Cell Apoptosis" J. Bio Chem , (1998), 5060-6.

Golshani-Hebroni, Shiva G. and Samuel P. Bessman, "Hexokinase Binding to Mitochondria: A Basis . . . ", Journal of Bioenergetics and Biomembranes, vol. 29, No. 4, pp. 331-338, 1997.

González-Barroso, M. Mar et al., "The Uncoupling Protein UCP1 Does Not . . . ", Journal of Biological Chemistry, vol. 273, No. 25, pp. 15528-15532, Jun. 19, 1998.

Gorer, P.A., "The Genetic and Antigenic Basis of Tumour Transplantation", Journal of Pathology, Vol. XLIV, pp. 691-697.

Gray, Michael W. et al., "Mitochondrial Evolution", Science, vol. 283, pp. 1476-1481, Mar. 5, 1999.

Greiner, Erich F. et al., "Glucose Is Essential for Proliferation and . . . ", Journal of Biological Chemistry, vol. 269, No. 50, pp. 31484-31490, Dec. 16, 1994.

Harper, Mary-Ellen and Martin D. Brand, "Use of Top-Down Elasticity Analysis . . . ", P.S.E.B.M., vol. 208, pp. 228-237, 1995.

Hatefi, Youssef and Mutsuo Yamaguchi, "Nicotinamide Nucleotide Transhydrogenase: A Model . . . ", FASEB J., vol. 10, pp. 444-452, Mar. 1996.

Haynes, Mark K. et al., "Helper-Inducer T-Lymphocytes Mediate Diabetes . . . ", Diabetes, vol. 36, pp. 877-881, Jul. 1987.

Hermesh, Orit et al., "Mitochondria Uncoupling by a Long Chain . . . ", Journal of Biological Chemistry, (1998) 273:7:3937-42.

Hess, B. et al., "Cooperation of Glycolytic Enzymes", pp. 149-167.

Himms-Hagen, Jean, "Brown Adipose Tissue Metabolism", Chp. 2, Obesity, Eds. Per Björntorp and Bernard N. Brodoff, J.B. Lippincott Company, Philadelphia, PA, 1992, pp. 15-34.

Hosokawa, H. et al., "Beta-Cell Hypersensitivity to Glucose . . . ", Diabetologia, vol. 40, pp. 392-397, 1997.

Huber, Sally A. and Barbara Pfaeffle, "Differential $TH_1$ and $TH_2$ Cell Responses . . . ", Journal of Virology, vol. 68, No. 8, pp. 5126-5132, Aug. 1994.

Huber, Sally A. et al., "Modulation of Cytokine Expression by CD4+. . . ", Journal of Virology, vol. 70, No. 5, pp. 3039-3044, May 1996.

Kang, Sang-Mo et al., "Fas Ligand Expression in Islets of . . . ", Nature Medicine, vol. 3, No. 7, pp. 738-743, Jul. 1997.

Kennedy, Eleanor D. et al., "Effects of Depletion of Mitochondrial . . . ", Diabetes, vol. 47, pp. 374-380, Mar. 1998.

Kiberstis, Paula A., "Mitochondria Make a Comeback", Science, vol. 283, p. 1475, Mar. 5, 1999.

Korshunov, Sergey S. et al., "Fatty Acids As Natural Uncouplers . . . ", FEBS Letters, vol. 435, pp. 215-218, 1998.

Larrouy, D. et al., "Kupffer Cells are a Dominant Site of Uncoupling Protein 2 Expression in Rat Liver", *Biochemical and Biophysical Research Communications*, 1997, pp. 760-764, vol. 235.

Le Meur, Marianne et al., "Correcting an Immune-Response Deficiency by . . . ", Nature, vol. 316, pp. 38-42, Jul. 4, 1985.

Le Meur, Marianne et al., "Restricted Assembly of MHC Class II . . . ", Journal of Immunology, vol. 142, No. 1, pp. 323-327, Jan. 1, 1989.

Lee, J., et al., "HLA-DR-Mediated Signals for Hematopoiesis and Induction of -Apoptosis Involve But Are Not Limited to a Nitric Oxide Pathway", *Blood*, (1997), 1:217-225.

Lefrancois, Leo et al., "Extrathymic Selection of TCR γδ+ T Cells . . . ", Cell, vol. 63, pp. 333-340, Oct. 19, 1990.

Lobato, M.N. et al., Intracellular antibodies and challenges facing their use as therapeutic agents. Trends Mol Med. Sep. 2003;9(9):390-6. Review.

Logan, Derek T., "A Glycyl Radical Site in . . . ", Science, vol. 283, pp. 1499-1504, Mar. 5, 1999.

Loudon, Robert P. et al., "An Attenuated Variant of Coxsackievirus . . . ", Journal of Virology, vol. 65, No. 11, pp. 5813-5819, Nov. 1991.

Luft, R. and B.R. Landau, "Mitochondrial Medicine", Journal of Internal Medicine, vol. 238, pp. 405-421, 1995.

Lühder, Fred et al., "Major Histocompatibility Complex Class II Molecules . . . ", J. Exp. Med., vol. 187, No. 3, pp. 379-387, Feb. 2, 1998.

Mackaness, George B., "The J. Burns Amberson Lecture—The Induction and Expression of Cell-Mediated Hypersensitivity in the Lung", American Review of Respiratory Disease, vol. 104, pp. 813-828, 1971.

Marzo, Isabel et al., "Bax and Adenine Nucleotide Translocator . . . ", Science, vol. 281, pp. 2027-2031, Sep. 25, 1998.

Mauricio, Dídac and Thomas Mandrup-Poulsen, "Apoptosis and the Pathogenesis of IDDM: A Question of Life and Death", Diabetes, vol. 47, pp. 1537-1543, Oct. 1998.

Meuer, Stefan and Klaus Resch, "Cellular Signalling in T Lymphocytes", Immunology Today, vol. 10, No. 8, pp. S23-S25, 1989 Supplement.

Meyer, T., et al., "Giant Cell Myocarditis due to Coxsackie B2 Virus Infection", Cardiology, 88:296-299, 1997.

Mieza, M., et al., "Selective Reduction of . . . Disease Development in Autoimmune-Prone Mice", The American Association of Immunologists, 4035-4040, 1996.

Morimoto, H. et al. "Overcoming Tumor Necrosis Factor and Drug Resistance of Humor Tumor Cell Lines by Combination Treatment with Anti-Fas Antibody and Drugs or Toxins," *Cancer Research*, 53(11), pp. 2591-2596, 1993.

Nakamoto, Yasunari et al., "Immune Pathogenesis of Hepatocellular Carcinoma", J. Exp. Med., vol. 188, No. 2, pp. 341-350, Jul. 20, 1998.

Nègre-Salvayre, Anne et al., "A Role for Uncoupling Protein-2 . . . ", FASEB J., vol. 11, pp. 809-815, 1997.

Newell, M. Karen et al., "Biochemical Characterization of Proteins that Co-purify . . . ", The Journal of Immunology, vol. 140, No. 6, pp. 1930-1938, Mar. 15, 1988.

Newell, M. Karen et al., "Death of Mature T Cells by Separate . . . ", Nature, vol. 347, pp. 286-289, Sep. 20, 1990.

Newell, M. Karen et al., "Ligation of Major Histocompatibility Complex . . . ", Proc. Natl. Acad. Sci. USA, vol. 90, pp. 10459-10463, Nov. 1993.

Palu, G. et al., In pursuit of new developments for gene therapy of human diseases. J Biotechnol. Feb. 5, 1999;68(1):1-13. Review.

Pecqueur, C. et al., "Uncoupling Protein 2: in vivo distribution, induction upon oxidative stress and evidence for translational regulation", *JBC Papers in Press Manuscript M006938200*, Nov. 29, 2000, pp. 1-41, The American Society for Biochemistry and Molecular Biology, Inc.

Pihl-Carey, K. BioWorld Today. vol. 10, pp. 1-2, 1999.

Posselt, Andrew M. et al., "Induction of Donor-Specific Unresponsiveness . . . ", Science, vol. 249, pp. 1293-1295, Sep. 4, 1990.

Reyes, Teresa M. and Christopher L. Coe, "The Proinflammatory Cytokine Network: Interactions . . . ", Am. J. Physiol. 274, pp. R139-R144, 1998.

Rustenbeck, Ingo et al., "Energetic Requirement of Insulin Secretion Distal to Calcium Influx", Diabetes, vol. 46, pp. 1305-1311, Aug. 1997.

Saraste, Matti, "Oxidative Phosphorylation at the Fin de Siècle", Science, vol. 283, pp. 1488-1493, Mar. 5, 1999.

Satoh, T., et al., "Changes in Mitochondrial Membrane Potential During Oxidative Stress-Induced Apoptosis in PC12 Cells", J. Neuroscience Rese., (1997), 413-420.

Scaffidi, et al., "Two CD95 (APO-1/Fas) Signaling Pathways", *The EMBO J.*, (1998), 1675-87.

Schattner, Elaine J. et al., "CD40 Ligation Induces Apo-1/Fas . . . ", J. Exp. Med., vol. 182, pp. 1557-1565, Nov. 1995.

Schild, Hansjörg et al., "The Nature of Major Histocompatibility Complex Recognition by γεT Cells", Cell, vol. 76, pp. 29-37, Jan. 14, 1994.

Schrezenmeier, Hubert et al., "Inactivation of a T Cell Receptor-Associated GTP-Binding . . . ", J. Exp. Med., vol. 168, pp. 817-822, Aug. 1988.

Sciorati, Clara et al., "Autocrine Nitric Oxide Modulates . . . ", Journal of Biological Chemistry, vol. 272, No. 37, pp. 23211-23215, Sep. 12, 1997.

Skerrett, P.J., "New Transplant Method Evades Immune Attack", Science, vol. 249, p. 1248, Sep. 1990.

Snell, George D., "Some Recollections of Peter Gorer and His Work on This Fiftieth Anniversary of His Discovery of H-2", Immunogenetics 24, pp. 339-340, 1986.

Snell, George D., "Studies in Histocompatibility", The Nobel Lectures in Immunology of Dec. 8, 1980, *Scandinavian Journal of Immunology* 36, pp. 513-526, 1992.

Stayton, P.S. et al., Molecular engineering of proteins and polymers for targeting and intracellular delivery of therapeutics. J Control Release. Mar. 1, 2000;65(1-2):203-20.

Street, D., et al., "Interferon-γ Enhances Susceptibility of Cervical Cancer Cells to Lysis by Tumor-Specifid Cytotoxic T Cells", *Gynecologic Oncology* 65, 265-272 (1997).

Summerfield, et al., "Lymphocyte Apoptosis during Classical Swine Fever Implication of Activation-Induced Cell Death", *J Virology*, (1998), 1853-1861.

Suzuki, Ivy and Pamela J. Fink, "Maximal Proliferation of Cytotoxic T Lymphocytes . . . ", J. Exp. Med., vol. 187, No. 1, pp. 123-128, Jan. 5, 1998.

Taneja, Veena et al., "Expression of the H2-E Molecule . . . ", International Immunology, vol. 9, No. 8, pp. 1213-1219, 1997.

Teruya, Masanori et al., "Pancreatic Islet Function in Nondiabetic and Diabetic BB Rats", Diabetes, vol. 42, pp. 1310-1317, Sep. 1993.

Tian, Jide and Daniel L. Kaufman, "Attenuation of Inducible Th2 Immunity . . . ", Journal of Immunology, vol. 161, pp. 5399-5403, 1998.

Truman, Jean-Philip et al., "HL A Class II Signaling Mediates . . . ", Experimental Hematology, vol. 24, pp. 1409-1415, 1996.

Truman, Jean-Philip et al., "HLA Class II—Mediated Death Is Induced . . . ", Blood, vol. 89, No. 6.

Vidal-Puig, A.J., "Uncoupling expectations", Nature Genetics, Dec. 2000, pp. 387-388, vol. 26, No. 4.

Wallace, Douglas C., "Mitochondrial Diseases in Man and Mouse", Science, vol. 283, pp. 1482-1488, Mar. 5, 1999.

Wilkens, Stephan and Roderick A. Capaldi, "ATP Synthase's Second Stalk Comes Into Focus", Nature, vol. 393, p. 29, May 7, 1998.

Yaffe, Michael P., "The Machinery of Mitochondrial Inheritance and Behavior", Science, vol. 283, pp. 1493-1497, Mar. 5, 1999.

Zhang, Weiguo et al., "LAT: The ZAP-70 Tyrosine Kinase . . . ", Cell, vol. 92, pp. 83-92, Jan. 9, 1998.

Zinkemagel, Rolf M. and Peter C. Doherty, "The Discovery of MHC Restriction", Immunology Today, vol. 18, No. 1, pp. 14-17, Jan. 1997.

Decaudin et al., Bcl-2 and Bcl-XL antagonize the mitochondrial dysfunction preceding nuclear apoptosis induced by chemotherapeutic agents. Cancer Res. Jan. 1, 1997;57(1):62-7.

Sokolove et al., Na+-independent release of Ca2+ from rat heart mitochondria. Induction by adriamycin aglycone. Biochem Pharmacol. Mar. 1, 1998;37(5):803-12.

Bates et al., A double-blind controlled trial of long chain n-3 polyunsaturated fatty acids in the treatment of multiple sclerosis.J Neurol Neurosurg Psychiatry. Jan. 1989;52(1):18-22.

Denardo et al., Effect of Lym-1 radioimmunoconjugate on refractory chronic lymphocytic leukemia. Cancer. Mar. 1, 1994;73(5):1425-32.

Finstad et al., Effect of n-3 and n-6 fatty acids on proliferation and differentiation of promyelocytic leukemic HL-60 cells. Blood. Dec. 1, 1994;84(11):3799-809.

Hu et al., A phase la clinical trial of LYM-1 monoclonal antibody serotherapy in patients with refractory B cell malignancies. Hematol Oncol. Mar.-Apr. 1989;7(2):155-66.

Jenski et al., Omega-3 fatty acid-containing liposomes in cancer therapy. Proc Soc Exp Biol Med. Dec. 1995;210(3):227-33.

Kremer et al., Effects of high-dose fish oil on rheumatoid arthritis after stopping nonsteroidal antiinflammatory drugs. Clinical and immune correlates. Arthritis Rheum. Aug. 1995;38(8):1107-14.

Quagliata et al., Immunotherapeutic approach to rheumatoid arthritis with anti-idiotypic antibodies to HLA-DR4. Isr J Med Sci. Feb.-Mar. 1993;29(2-3):154-9. Review.

Rose et al., Effects of dietary omega-3 fatty acids on human breast cancer growth and metastases in nude mice. J Natl Cancer Inst. Nov. 3, 1993;85(21):1743-7.

* cited by examiner

SEQUENCE LISTING

<160> NUMBER OF SEQ ID NOS: 19

<210> SEQ ID NO 1
<211> LENGTH: 924
<212> TYPE: DNA
<213> ORGANISM: Homo sapiens

<400> SEQUENCE: 1 atgggggggcc tgacagcctc ggacgtacac ccgaccctgg gggtccagct cttctcagct    60

```
ggaatagcgg cgtgcttggc ggacgtgatc accttcccgc tggacacggc caaagtccgg    120
ctccaggtcc aaggtgaatg cccgacgtcc agtgttatta ggtataaagg tgtcctggga    180
acaatcaccg ctgtggtaaa aacagaaggg cggatgaaac tctacagcgg gctgcctgcg    240
gggcttcagc ggcaaatcag ctccgcctct ctcaggatcg gcctctacga cacggtccag    300
gagttcctca ccgcagggaa agaaacagca cctagtttag gaagcaagat tttagctggt    360
ctaacgactg gaggagtggc agtattcatt gggcaaccca cagaggtcgt gaaagtcaga    420
cttcaagcac agagccatct ccacggaatc aaacctcgct acacgggac ttataatgcg     480 tacagaataa tagcaacaac cgaaggcttg acgggtcttt ggaaagggac tactcccaat    540
ctgatgagaa gtgtcatcat caattgtaca gagctagtaa catatgatct aatgaaggag    600
gcctttgtga aaacaacat attagcagat gacgtcccct gccacttggt gtcggctctt     660
atcgctggat tttgcgcaac agctatgtcc tccccggtgg atgtagtaaa accagattt     720 attaattctc caccaggaca gtacaaaagt gtgcccaact gtgcaatgaa agtgttcact    780
aacgaaggac caacggcttt cttcaagggg ttggtacctt ccttcttgcg acttggatcc    840
tggaacgtca ttatgtttgt gtgctttgaa caactgaaac gagaactgtc aaagtcaagg    900
cagactatgg actgtgccac ataa                                           924
```

```
<210> SEQ ID NO 2
<211> LENGTH: 307
<212> TYPE: PRT
<213> ORGANISM: Homo sapiens

<400> SEQUENCE: 2

Met Gly Gly Leu Thr Ala Ser Asp Val His Pro Thr Leu Gly Val Gln
1               5                   10                  15

Leu Phe Ser Ala Gly Ile Ala Ala Cys Leu Ala Asp Val Ile Thr Phe
            20                  25                  30

Pro Leu Asp Thr Ala Lys Val Arg Leu Gln Val Gln Gly Glu Cys Pro
        35                  40                  45

Thr Ser Ser Val Ile Arg Tyr Lys Gly Val Leu Gly Thr Ile Thr Ala
    50                  55                  60

Val Val Lys Thr Glu Gly Arg Met Lys Leu Tyr Ser Gly Leu Pro Ala
65                  70                  75                  80

Gly Leu Gln Arg Gln Ile Ser Ser Ala Ser Leu Arg Ile Gly Leu Tyr
                85                  90                  95

Asp Thr Val Gln Glu Phe Leu Thr Ala Gly Lys Glu Thr Ala Pro Ser
            100                 105                 110

Leu Gly Ser Lys Ile Leu Ala Gly Leu Thr Thr Gly Gly Val Ala Val
        115                 120                 125

Phe Ile Gly Gln Pro Thr Glu Val Val Lys Val Arg Leu Gln Ala Gln
    130                 135                 140

Ser His Leu His Gly Ile Lys Pro Arg Tyr Thr Gly Thr Tyr Asn Ala
145                 150                 155                 160

Tyr Arg Ile Ile Ala Thr Thr Glu Gly Leu Thr Gly Leu Trp Lys Gly
                165                 170                 175

Thr Thr Pro Asn Leu Met Arg Ser Val Ile Ile Asn Cys Thr Glu Leu
            180                 185                 190

Val Thr Tyr Asp Leu Met Lys Glu Ala Phe Val Lys Asn Asn Ile Leu
        195                 200                 205

Ala Asp Asp Val Pro Cys His Leu Val Ser Ala Leu Ile Ala Gly Phe
```

```
              210                 215                 220
Cys Ala Thr Ala Met Ser Ser Pro Val Asp Val Lys Thr Arg Phe
225                 230                 235                 240

Ile Asn Ser Pro Pro Gly Gln Tyr Lys Ser Val Pro Asn Cys Ala Met
                245                 250                 255

Lys Val Phe Thr Asn Glu Gly Pro Thr Ala Phe Phe Lys Gly Leu Val
                260                 265                 270

Pro Ser Phe Leu Arg Leu Gly Ser Trp Asn Val Ile Met Phe Val Cys
            275                 280                 285

Phe Glu Gln Leu Lys Arg Glu Leu Ser Lys Ser Arg Gln Thr Met Asp
        290                 295                 300

Cys Ala Thr
305

<210> SEQ ID NO 3
<211> LENGTH: 1105
<212> TYPE: DNA
<213> ORGANISM: Homo sapiens

<400> SEQUENCE: 3
gttcctctat ctcgtcttgt tgctgattaa aggtgcccct gtctccagtt tttctccatc    60
tcctgggacg tagcaggaaa tcagcatcat ggttgggttc aaggccacag atgtgccccc   120
tactgccact gtgaagtttc ttggggctgg cacagctgcc tgcatcgcag atctcatcac   180
ctttcctctg gatactgcta aagtccggtt acagatccaa ggagaaagtc aggggccagt   240
gcgcgctaca gccagcgccc agtaccgcgg tgtgatgggc accattctga ccatggtgcg   300
tactgagggc ccccgaagcc tctacaatgg gctggttgcc ggcctgcagc gccaaatgag   360 cttttgcctct gtccgcatcg gcctgtatga ttctgtcaaa cagttctaca ccaagggctc   420
tgagcatgcc agcattggga gccgcctcct agcaggcagc accacaggtg ccctggctgt   480
ggctgtggcc cagcccacgg atgtggtaaa ggtccgattc caagctcagg cccgggctgg   540
aggtggtcgg agataccaaa gcaccgtcaa tgcctacaag accattgccc gagaggaagg   600
gttccggggc ctctggaaag ggacctctcc caatgttgct cgtaatgcca ttgtcaactg   660
tgctgagctg gtgaccctatg acctcatcaa ggatgccctc ctgaaagcca acctcatgac   720
agatgacctc ccttgccact tcacttctgc ctttggggca ggcttctgca ccactgtcat   780
cgcctcccct gtagacgtgg tcaagacgag atacatgaac tctgccctgg ccagtacag   840 tagcgctggc cactgtgccc ttaccatgct ccagaaggag gggcccccgag ccttctacaa   900 agggttcatg ccctcctttc tccgcttggg ttcctggaac gtggtgatgt tcgtcaccta   960
tgagcagctg aaacgagccc tcatggctgc ctgcacttcc cgagaggctc ccttctgagc  1020
ctctcctgct gctgacctga tcacctctgg ctttgtctct agccgggcca tgctttcctt  1080
ttcttccttc tttctcttcc ctccg                                        1105

<210> SEQ ID NO 4
<211> LENGTH: 309
<212> TYPE: PRT
<213> ORGANISM: Homo sapiens

<400> SEQUENCE: 4

Met Val Gly Phe Lys Ala Thr Asp Val Pro Pro Thr Ala Thr Val Lys
1               5                   10                  15

Phe Leu Gly Ala Gly Thr Ala Ala Cys Ile Ala Asp Leu Ile Thr Phe
            20                  25                  30
```

Pro Leu Asp Thr Ala Lys Val Arg Leu Gln Ile Gln Gly Glu Ser Gln
         35                  40                  45

Gly Pro Val Arg Ala Thr Ala Ser Ala Gln Tyr Arg Gly Val Met Gly
     50                  55                  60

Thr Ile Leu Thr Met Val Arg Thr Glu Gly Pro Arg Ser Leu Tyr Asn
 65                  70                  75                  80

Gly Leu Val Ala Gly Leu Gln Arg Gln Met Ser Phe Ala Ser Val Arg
                 85                  90                  95

Ile Gly Leu Tyr Asp Ser Val Lys Gln Phe Tyr Thr Lys Gly Ser Glu
                100                 105                 110

His Ala Ser Ile Gly Ser Arg Leu Leu Ala Gly Ser Thr Thr Gly Ala
            115                 120                 125

Leu Ala Val Ala Val Ala Gln Pro Thr Asp Val Val Lys Val Arg Phe
        130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
                180                 185                 190

Glu Leu Val Thr Tyr Asp Leu Ile Lys Asp Ala Leu Leu Lys Ala Asn
            195                 200                 205

Leu Met Thr Asp Asp Leu Pro Cys His Phe Thr Ser Ala Phe Gly Ala
        210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
            260                 265                 270

Phe Met Pro Ser Phe Leu Arg Leu Gly Ser Trp Asn Val Val Met Phe
        275                 280                 285

Val Thr Tyr Glu Gln Leu Lys Arg Ala Leu Met Ala Ala Cys Thr Ser
    290                 295                 300

Arg Glu Ala Pro Phe
305

<210> SEQ ID NO 5
<211> LENGTH: 1132
<212> TYPE: DNA
<213> ORGANISM: Homo sapiens

<400> SEQUENCE: 5
tcctgggatg gagccctagg gagcccctgt gctgccsctg ccgtggcagg actcacagcc      60
ccaccgctgc actgaagccc agggctgtgg agcagcctct ctccttggac ctcctctcgg     120
ccctaaaggg actgggcaga gccttccagg actatggttg gactgaagcc ttcagacgtg     180
cctcccacca tggctgtgaa gttcctgggg gcaggcacag cagcctgttt tgctgacctc     240
gttacctttc cactgacaca gccaaggtc cgcctgcaga tccaggggga gaaccaggcg     300
gtccagacgg cccggctcgt gcagtaccgt ggcgtgctgg caccatcct gaccatggtg     360 cggactgagg gtccctgcag ccctacaat gggctggtgg ccggcctgca gcgccagatg     420
agcttcgcct ccatccgcat cggcctctat gactccgtca gcaggtgta cacccccaaa     480

```
ggcgcggaca actccagcct cactacccgg attttggccg gctgcaccac aggagccatg    540
gcggtgacct gtgcccagcc cacagatgtg gtgaaggtcc gatttcaggc cagcatacac    600
ctcgggccat ccaggagcga cagaaaatac agcgggacta tggacgccta cagaaccatc    660
gccagggagg aaggagtcag gggcctgtgg aaaggaactt tgcccaacat catgaggaat    720
gctatcgtca actgtgctga ggtggtgacc tacgacatcc tcaaggagaa gctgctggac    780
taccacctgc tcactgacaa cttcccctgc cactttgtct ctgcctttgg agccggcttc    840
tgtgccacag tggtggcctc cccggtggac gtggtgaaga cccggtatat gaactcacct    900
ccaggccagt acttcagccc cctcgactgt atgataaaga tggtggccca ggagggcccc    960
acagccttct acaaggggtg agcctcctcc tgcctccagc actccctccc agagaacagg   1020
ggcttctttc ttttcgaatg tggctaccgt gggtcaacct gggatgtagc ggtgaagagt   1080
acagatgtaa atgccacaaa gaagaagttt aaaaaaccat gcaaaaaaaa aa            1132
```

<210> SEQ ID NO 6
<211> LENGTH: 275
<212> TYPE: PRT
<213> ORGANISM: Homo sapiens

<400> SEQUENCE: 6

```
Met Val Gly Leu Lys Pro Ser Asp Val Pro Thr Met Ala Val Lys
 1               5                  10                  15

Phe Leu Gly Ala Gly Thr Ala Ala Cys Phe Ala Asp Leu Val Thr Phe
                20                  25                  30

Pro Leu Asp Thr Ala Lys Val Arg Leu Gln Ile Gln Gly Glu Asn Gln
            35                  40                  45

Ala Val Gln Thr Ala Arg Leu Val Gln Tyr Arg Gly Val Leu Gly Thr
        50                  55                  60

Ile Leu Thr Met Val Arg Thr Glu Gly Pro Cys Ser Pro Tyr Asn Gly
65                  70                  75                  80

Leu Val Ala Gly Leu Gln Arg Gln Met Ser Phe Ala Ser Ile Arg Ile
                85                  90                  95

Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
        115                 120                 125

Met Ala Val Thr Cys Ala Gln Pro Thr Asp Val Val Lys Val Arg Phe
130                 135                 140

Gln Ala Ser Ile His Leu Gly Pro Ser Arg Ser Asp Arg Lys Tyr Ser
                145                 150                 155             160

Gly Thr Met Asp Ala Tyr Arg Thr Ile Ala Arg Glu Glu Gly Val Arg
            165                 170                 175

Gly Leu Trp Lys Gly Thr Leu Pro Asn Ile Met Arg Asn Ala Ile Val
        180                 185                 190

Asn Cys Ala Glu Val Val Thr Tyr Asp Ile Leu Lys Glu Lys Leu Leu
    195                 200                 205

Asp Tyr His Leu Leu Thr Asp Asn Phe Pro Cys His Phe Val Ser Ala
210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
```

```
                260                 265                 270
Tyr Lys Gly
        275

<210> SEQ ID NO 7
<211> LENGTH: 25
<212> TYPE: PRT
<213> ORGANISM: Unknown
<220> FEATURE:
<223> OTHER INFORMATION: P-Cadherin membrane attachment domain

<400> SEQUENCE: 7

Phe Ile Leu Pro Ile Leu Gly Ala Val Leu Ala Leu Leu Leu Leu Leu
1               5                   10                  15

Thr Leu Leu Ala Leu Leu Leu Leu Val
            20                  25

<210> SEQ ID NO 8
<211> LENGTH: 26
<212> TYPE: PRT
<213> ORGANISM: Unknown
<220> FEATURE:
<223> OTHER INFORMATION: CD2 membrane attachment domain

<400> SEQUENCE: 8

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25

<210> SEQ ID NO 9
<211> LENGTH: 22
<212> TYPE: PRT
<213> ORGANISM: Unknown
<220> FEATURE:
<223> OTHER INFORMATION: CD40 membrane attachment domain

<400> SEQUENCE: 9

Ala Leu Val Val Ile Pro Ile Ile Phe Gly Ile Leu Phe Ala Ile Leu
1               5                   10                  15

Leu Val Leu Val Phe Ile
            20

<210> SEQ ID NO 10
<211> LENGTH: 20
<212> TYPE: PRT
<213> ORGANISM: Unknown
<220> FEATURE:
<223> OTHER INFORMATION: Contactin membrane attachment domain

<400> SEQUENCE: 10

Ile Ser Gly Ala Thr Ala Gly Val Pro Thr Leu Leu Leu Gly Leu Val
1               5                   10                  15

Leu Pro Ala Pro
            20

<210> SEQ ID NO 11
<211> LENGTH: 24
<212> TYPE: PRT
<213> ORGANISM: Unknown
<220> FEATURE:
<223> OTHER INFORMATION: IL-4 receptor membrane attachment domain

<400> SEQUENCE: 11
```

-continued

```
Leu Leu Leu Gly Val Ser Val Ser Cys Ile Val Ile Leu Ala Val Cys
1               5                   10                  15

Leu Leu Cys Tyr Val Ser Ile Thr
            20

<210> SEQ ID NO 12
<211> LENGTH: 24
<212> TYPE: PRT
<213> ORGANISM: Unknown
<220> FEATURE:
<223> OTHER INFORMATION: Mannose receptor membrane attachment domain
<400> SEQUENCE: 12

Val Ala Gly Val Val Ile Ile Val Ile Leu Leu Ile Leu Thr Gly Ala
1               5                   10                  15

Gly Leu Ala Ala Tyr Phe Phe Tyr
            20

<210> SEQ ID NO 13
<211> LENGTH: 25
<212> TYPE: PRT
<213> ORGANISM: Unknown
<220> FEATURE:
<223> OTHER INFORMATION: M-CSF receptor membrane attachment domain
<400> SEQUENCE: 13

Phe Leu Phe Thr Pro Val Val Val Ala Cys Met Ser Ile Met Ala Leu
1               5                   10                  15

Leu Leu Leu Leu Leu Leu Leu Leu Leu
            20                  25

<210> SEQ ID NO 14
<211> LENGTH: 30
<212> TYPE: PRT
<213> ORGANISM: Unknown
<220> FEATURE:
<223> OTHER INFORMATION: PDGFR .beta. chain membrane attachment domain
<400> SEQUENCE: 14

Val Val Val Ile Ser Ala Ile Leu Ala Leu Val Val Leu Thr Ile Ile
1               5                   10                  15

Ser Leu Ile Ile Leu Ile Met Leu Trp Gln Lys Lys Pro Arg
            20                  25                  30

<210> SEQ ID NO 15
<211> LENGTH: 26
<212> TYPE: PRT
<213> ORGANISM: Unknown
<220> FEATURE:
<223> OTHER INFORMATION: PDGFR .alpha. chain membrane attachment domain
<400> SEQUENCE: 15

Glu Leu Thr Val Ala Ala Ala Val Leu Val Leu Leu Val Ile Val Ser
1               5                   10                  15

Ile Ser Leu Ile Val Leu Val Val Thr Trp
            20                  25

<210> SEQ ID NO 16
<211> LENGTH: 24
<212> TYPE: PRT
<213> ORGANISM: Unknown
<220> FEATURE:
<223> OTHER INFORMATION: P-Selectin membrane attachment domain
<400> SEQUENCE: 16
```

```
Leu Thr Tyr Phe Gly Gly Ala Val Ala Ser Thr Ile Gly Leu Ile Met
1               5                   10                  15

Gly Gly Thr Leu Leu Ala Leu Leu
            20

<210> SEQ ID NO 17
<211> LENGTH: 34
<212> TYPE: PRT
<213> ORGANISM: Unknown
<220> FEATURE:
<223> OTHER INFORMATION: Rat Thy-1

<400> SEQUENCE: 17

Val Lys Cys Gly Gly Ile Ser Leu Leu Val Gln Asn Thr Ser Trp Leu
1               5                   10                  15

Leu Leu Leu Leu Leu Ser Leu Ser Phe Leu Gln Ala Thr Asp Phe Ile
            20                  25                  30

Ser Leu

<210> SEQ ID NO 18
<211> LENGTH: 23
<212> TYPE: PRT
<213> ORGANISM: Unknown
<220> FEATURE:
<223> OTHER INFORMATION: TNFR-1 membrane attachment domain

<400> SEQUENCE: 18

Thr Val Leu Leu Pro Leu Val Ile Phe Phe Gly Leu Cys Leu Leu Ser
1               5                   10                  15

Leu Leu Phe Ile Gly Leu Met
            20

<210> SEQ ID NO 19
<211> LENGTH: 23
<212> TYPE: PRT
<213> ORGANISM: Unknown
<220> FEATURE:
<223> OTHER INFORMATION: VCAM-1 membrane attachment domain

<400> SEQUENCE: 19

Leu Leu Val Leu Tyr Phe Ala Ser Ser Leu Ile Ile Pro Ala Ile Gly
1               5                   10                  15

Met Ile Ile Tyr Phe Ala Arg
            20
```

METHODS AND PRODUCTS FOR MANIPULATING UNCOUPLING PROTEIN EXPRESSION

RELATED APPLICATIONS

This application is a divisional of U.S. application Ser. No. 09/599,760, filed Jun. 22, 2000, now pending, and claims the benefit under 35 U.S.C. §119(e) from U.S. provisional application Ser. No. 60/140,574, filed Jun. 23, 1999, the entire contents of which is hereby incorporated by reference.

FIELD OF THE INVENTION

The present invention relates to the discovery that the cellular location of uncoupling protein (UCP) is altered in some cell types under differing metabolic states. In particular, the invention relates to methods and products for manipulating UCP expression in various membranes. The invention also relates to methods of sensitizing resistant tumor cells to cytotoxic treatments by inducing expression of UCP in the plasma membrane. The invention also relates to kits, compositions and screening assays.

BACKGROUND OF THE INVENTION

Normal tissue develops and is maintained by processes of cell division and cell death. In many diseases, such as cancer, diabetes mellitus Type I, and autoimmune disease, the normal balance between cell division and cell death is disrupted causing either a rapid growth of unwanted and potentially dangerous cells or a loss of cells which are essential to maintaining the functions of tissue.

Cell division occurs by a process known as mitosis. During mitosis dividing cells use glucose cytolytically at an increased rate as the primary source for energy (ATP) production in a process referred to as glycolysis (Brand, K. A., and U. Hermfisse. 1997. *Aerobic glycolysis by proliferating cells: a protective strategy against reactive oxygen species. Faseb J* 11, no. 5:388-95). Glycolysis occurs in the cytosol and is required for mitochondrial energy production. An increased rate of glycolysis occurs when cells divide, providing more of the ATP from cytosolic glycolysis. Mitochondrial synthesis of ATP proceeds through coupling of electron transport-dependent oxido-reductive reactions to ATP synthetase (oxidative phosphorylation) (Harper, M. E. 1997. *Obesity research continues to spring leaks. Clinical Investigations in Medicine* 20, no. 4.239-244). During this process, a proton gradient is generated by the pumping of protons out of the mitochondria (Himms-Hagen, J. 1992. *Brown Adipose Tissue. Obesity*, eds. P. Bjorntorp and B. N. Brodoff 1 vols. J. B. Lippincott, Philadelphia. 1 pp), increasing mitochondrial membrane potential. Uncoupling proteins (UCPs) reversibly uncouple oxidative phosphorylation from electron transport in the mitochondria and thereby can decrease mitochondrial membrane potential (Harper, M. E. 1997. *Obesity research continues to spring leaks. Clinical Investigations in Medicine* 20, no. 4:239-244). Elevating glucose concentrations can increase mitochondrial membrane potential (Harper, M. E. 1997. *Obesity research continues to spring leaks. Clinical Investigations in Medicine* 20, no. 4:239-244). UCP and methods of regulating or modulating UCP have been described in many publications, including for example U.S. Pat. Nos. 5,849,514; 5,849,581; 5,846,779; and 5,453,270.

Cell death is a physiologic process that ensures homeostasis is maintained between cell production and cell turnover in self-renewing tissues and is essential to the proper functioning of the immune system. Physiological cell death occurs through the processes of apoptosis and necrosis. The boundaries between these processes, once thought to be distinct, have blurred with the explosion of information on the role of cell death in development, tissue modeling, regenerative processes, and in the immune system. However, it is widely accepted that necrotic cell death (sometimes called oncosis) typically results in the osmotic rupture of a cell, followed by an inflammatory response, while apoptotic death involves cell shrinkage, fragmentation of the cell, and phagocytosis of the fragments often without inflammation. Most cells die in a form of suicide characteristically apoptotic and tightly regulated by complex signals (Zakeri, Z., W. Bursch, M. Tenniswood, and R. A. Lockshin. 1995. *Cell Death: Programmed, apoptosis, necrosis, or other. Cell Death and Differentiation* 2:87-96). Apoptotic cell death is particularly important in the reticulo-endothelial system where the balance between mitosis and cell death may determine the effectiveness and the nature of an immune response (Zakeri, Z., W. Bursch, M. Tenniswood, and R. A. Lockshin. 1995. *Cell Death: Programmed, apoptosis, necrosis, or other. Cell Death and Differentiation* 2:87-96). Failure results in autoimmune disease or in a lack of immune surveillance.

Inappropriate cell division or cell death results in serious life-threatening diseases. Diseases associated with increased cell division include cancer and atherosclerosis. Disease resulting from increased cell death include AIDS, neurodegenerative diseases (e.g., Alzheimer's disease, Parkinson's disease, amyotrophic lateral sclerosis, retinitis pigmentosa), aplastic anemia, atherosclerosis (e.g., myocardial infarction, stroke, reperfusion injury), and toxin induced liver disease. Many methods for treating these disorders have been proposed Although these diseases share the common physiological trait of either excess cell division or premature cell death, strategies for identifying potential therapeutic treatments have been individualized rather than searching for a common mechanism. It would be desirable to identify a common mechanism by which cell division could be interrupted or cell death could be promoted to treat all of these diseases.

SUMMARY OF THE INVENTION

The invention involves in some aspects the finding that uncoupling protein (UCP) is present in membranes other than the mitochondria. For instance, it has been discovered that UCP is present in the plasma membrane of rapidly dividing cells. It was found according to the invention that the UCP in the plasma membrane plays an important role in the signal which determines whether a cell will undergo cellular division, cellular differentiation or cellular death. This finding has important implications for treating diseases associated with excessive cellular division, aberrant differentiation, and premature cellular death, e.g., for the treatment of cancers, autoimmune disease, degenerative diseases, regeneration etc. It has also been discovered that UCP is present in lysosomal membranes.

Several cell surface proteins have previously been identified as cell death proteins. These proteins are believed to be involved in initiating a signal which instructs the cell to die. Cell death proteins include for example Fas/CD95 (Trauth et al., *Science* 245:301, 1989), tumor necrosis factor receptors, immune cell receptors such as CD40, OX40, CD27 and 4-1BB (Smith et al., *Cell* 76:959, 1994), and RIP (U.S. Pat. No. 5,674,734). These proteins are believed to be important mediators of cell death. These mediators, however, do not always instruct a cell to die. In some cases these mediators actually instruct a cell to undergo cell division. The intracellular environment and particularly the status of the proton motor force and source of fuel for mitochondrial metabolism determines whether stimulation of the cell death protein will lead to a signal for death or cell division (co-pending U.S. patent application Ser. No. 09/277,575 incorporated herein by reference).

The invention involves the finding that another cell surface protein, UCP, also can regulate cell division by manipulating the manner in which the cell processes and utilizes energy. It was discovered according to the invention that UCP is present on the plasma membrane of rapidly dividing cells but is not on the plasma membrane of growth arrested and chemotherapy resistant tumor cells. These findings have important implications on the ability to regulate cell division as well as sensitivity and resistance to chemotherapeutic agents.

In one aspect the invention is a method for inhibiting plasma membrane UCP expression in a rapidly dividing cell. The method includes the step of contacting a rapidly dividing cell with a plasma membrane targeted UCP inhibitor to inhibit plasma membrane UCP expression. In one embodiment the method is a method for preventing cell division in a rapidly dividing cell and wherein the loss of UCP activity in the plasma membrane of the rapidly dividing cell prevents cell division.

The invention in another aspect is a method for inhibiting plasma membrane UCP expression in a cell by contacting a cell with a plasma membrane UCP inhibitor to inhibit plasma membrane UCP expression. In one embodiment the plasma membrane UCP inhibitor is selected from the group consisting of a UCP binding peptide or molecule, an anti-UCP antibody, a hydrophobic nucleotide analog, UCP-inhibitor conjugated to a membrane attachment domain, and a non-omega-3 fatty acid.

The method may be used to induce cell death of a tumor cell. Thus in one embodiment the rapidly dividing cell is a tumor cell. The tumor cell may be in a subject, in which case the plasma membrane targeted UCP inhibitor is administered in vivo or ex vivo. The subject may also be administered a cytotoxic anti-tumor therapy.

The method may also be performed on other rapidly dividing cells such as, but not limited to a lymphocyte, a pancreatic β cell, or a bacteria.

In some embodiments the plasma membrane targeted UCP inhibitor is a UCP binding peptide or molecule. In other embodiments the plasma membrane targeted UCP inhibitor is an anti-UCP antibody. In yet other embodiments it is selected from the group consisting of a UCP antisense and dominant negative UCP. In yet another embodiment the plasma membrane targeted UCP inhibitor is a nucleotide analog. When the rapidly dividing cell is a tumor cell and the plasma membrane targeted UCP inhibitor is a nucleotide analog the nucleotide analog may be, in some embodiments, targeted specifically to the plasma membrane UCP. This can be accomplished by linking the nucleotide analog to a cell surface targeting molecule or by manipulating the nucleotide analog or the cell to prevent uptake of the nucleotide analog by the cell. When the rapidly dividing cell is a lymphocyte, a pancreatic β cell, or a bacteria and the plasma membrane targeted UCP inhibitor is a nucleotide analog the nucleotide analog the nucleotide analog may be delivered directly to the cell or may be targeted specifically to the plasma membrane UCP. In one embodiment it is targeted specifically to the plasma membrane UCP.

In another aspect the invention is a composition of an UCP associated with a plasma or lysosomal membrane targeting molecule. The composition may optionally include a colloidal dispersion system, wherein the UCP and the plasma or lysosomal membrane targeting molecule are incorporated into the colloidal dispersion system. In one embodiment the colloidal dispersion system is a liposome.

In another aspect of the invention a composition of an UCP inhibitor associated with a plasma or lysosomal membrane targeting molecule is provided. The composition may optionally include a colloidal dispersion system, wherein the UCP inhibitor and the plasma or lysosomal membrane targeting molecule are incorporated into the colloidal dispersion system. In one embodiment the colloidal dispersion system is a liposome.

In some embodiments of the composition the plasma or lysosomal membrane targeted UCP inhibitor is a UCP binding peptide or molecule. In other embodiments the plasma or lysosomal membrane targeted UCP inhibitor is an anti-UCP antibody or antibody fragment. In yet other embodiments it is selected from the group consisting of a UCP antisense and dominant negative UCP. Optionally the UCP inhibitor is an anti-UCP antibody conjugated to an anti-cell surface molecule antibody. In yet another embodiment the plasma or lysosomal membrane targeted UCP inhibitor is a nucleotide analog.

A method for inducing cellular division in a growth arrested cell is provided according to another aspect of the invention. The method includes the step of inducing expression of UCP in a plasma membrane of a growth arrested cell under conditions in which the presence of the UCP within the plasma membrane of the growth arrested cell causes cell division of the growth arrested cell. In another aspect, the invention is a method for sensitizing a resistant tumor cell to a cytotoxic therapy. The method may be performed by inducing expression of UCP in the plasma membrane of a resistant tumor cell. The presence of the UCP within the plasma membrane of the resistant tumor cell renders the resistant tumor cell sensitive to cytotoxic therapy.

In one embodiment the method involves the step of contacting the growth arrested cell or resistant tumor cell with an UCP associated with a plasma membrane targeting molecule. In another embodiment the growth arrested cell or resistant tumor cell is a melanoma cell.

The invention also includes screening assays and kits relating to the above-described methods and compositions. One screening assay of the invention is a method for screening a tumor cell of a subject for susceptibility to treatment with a chemotherapeutic agent. The method involves the steps of isolating a tumor cell from a subject; and detecting the presence of a UCP molecule in the plasma membrane of the tumor cell, wherein the presence of the UCP molecule in the plasma membrane indicates that the tumor cell is susceptible to treatment with a chemotherapeutic agent.

In one embodiment the method comprises the step of contacting the tumor cell with a detection reagent that selectively binds to the plasma membrane UCP molecule to detect the presence of the plasma membrane UCP molecule. The plasma membrane UCP molecule may be a plasma membrane UCP mRNA. In that case the detection reagent is a nucleic acid that selectively hybridizes to the plasma membrane UCP mRNA and wherein the cell is contacted with the detection reagent under conditions that permit selective hybridization of the nucleic acid to the plasma membrane UCP mRNA. The plasma membrane UCP molecule may also be a plasma membrane UCP polypeptide. In that case the detection reagent is a plasma membrane UCP binding peptide and wherein the plasma membrane UCP polypeptide is contacted with the detection reagent under conditions that permit selective binding of the plasma membrane UCP binding peptide to the plasma membrane UCP polypeptide. In one embodiment the plasma membrane UCP binding peptide is an anti-plasma membrane UCP polypeptide antibody. In another embodiment the presence of the plasma membrane UCP polypeptide is detected by contacting the tumor cell with a plasma membrane UCP binding peptide attached to a solid support.

According to another aspect of the invention a method for screening a subject for the presence of rapidly dividing cells is provided. The method includes the steps of isolating a sample of cells from a subject; and, detecting the presence of a plasma membrane UCP molecule in the plasma membrane of the cell, wherein the presence of the plasma membrane UCP molecule is indicative of a rapidly dividing cell.

A kit for screening a tumor cell of a subject for susceptibility to treatment with a chemotherapeutic agent is provided according to another aspect of the invention. The kit includes a container housing a UCP molecule detection reagent; and instructions for using the UCP molecule detection reagent for detecting the presence of a UCP molecule on the plasma membrane of the tumor cell, wherein the presence of the plasma membrane UCP molecule indicates that the cell is susceptible to treatment with a chemotherapeutic agent.

In one embodiment the kit also includes a container housing a chemotherapeutic agent. In other embodiments the kit includes a panel of chemotherapeutic agents, housed in separate compartments. In yet another embodiment the kit includes a UCP molecule detection reagent attached to a solid surface.

The invention in other aspects relates to a composition of a plasma membrane targeted UCP inhibitor. In one embodiment the UCP inhibitor is a nucleotide or nucleotide analog. In another embodiment the nucleotide analog is a purine analog. Preferably the purine analog is selected from the group consisting of guanosine diphosphate, 8-oxo-Adenosine, 8-oxo-Guanosine, 8-fluoro-Adenosine, 8-fluoro-Guanosine, 8-methoxy-Adenosine, 8-methoxy-Guanosine, 8-aza-Adenosine and 8-aza-Guanosine, azacitidine, Fludarabine phosphate, 6-MP, 6-TG, azathiprine, allopurinol, acyclovir, gancylovir, deoxycoformycin, and arabinosyladienine (ara-A), guanosine diphosphate fucose, guanosine diphosphate-2-fluorofucose, guanosine diphosphate-.beta.L-2-aminofucose, guanosine diphosphate-D-arabinose and 2-aminoadenosine.

In another embodiment the nucleotide analog is a pyrimidine analog. Preferably the pyrimidine analog is selected from the group consisting of uracil, thymine, cytosine, 5-fluorouracil, 5-chlorouracil, 5-bromouracil, dihydrouracil, 5-methylcytosine, 5-propynylthymine, 5-propynyluracil and 5-propynylcytosine, 5-fluorocytosine, Floxuridine, uridine, thymine, 3'-azido-3'-deoxythymidine, 2-fluorodeoxycytidine, 3-fluoro-3'-deoxythymidine; 3'-dideoxycytidin-2'-ene; and 3'-deoxy-3'-deoxythymidin-2'-ene, and cytosine arabinoside.

In yet other embodiments the composition includes a pharmaceutically acceptable carrier. The composition may also include a colloidal dispersion system, wherein the plasma membrane UCP inhibitor is incorporated into the colloidal dispersion system. Optionally the colloidal dispersion system is a liposome.

According to some embodiments the plasma membrane UCP inhibitor includes a hydrophobic moiety and optionally the plasma membrane UCP inhibitor is a modified nucleotide analog conjugated to a hydrophobic moiety. In other embodiments the plasma membrane UCP inhibitor includes a membrane attachment domain, which is optionally conjugated to a nucleotide or nucleotide analog. In preferred embodiments the membrane attachment domain is a Type I membrane attachment domain, Type II membrane attachment domain, or Type III membrane attachment domain. In other embodiments the membrane attachment domain is selected from the group consisting of P-Cadherin (FILPILGAVLALLLLLTL-LALLLLV); CD2 (IYLIIGICGGGSLLMVFVALLVFYIT); CD40 (ALVVIPIIFGILFAILLVLVFI); Contactin (ISGAT-AGVPTLLLGLVLPAP); IL-4 receptor (LLLGVSVS-CIVILAVCLLCYVSIT); Mannose receptor (VAGVVIIVIL-LILTGAGLAAYFFY); M-CSF receptor (FLFTPVVVACMSIMALLLLLLLLLL); PDGFR .beta. chain (VVVISAILALVVLTIISLIILIMLWQKKPR); PDGFR .alpha. chain (ELTVAAAVLVLLVIVSISLIVLV-VTW); P-Selectin (LTYFGGAVASTIGLIMGGTLLALL); Rat Thy-1 (VKCGGISLLVQNTSWLLLLLLSLS-FLQATDFISL); TNFR-1 (TVLLPLVIFFGLCLLSLL-FIGLM); and VCAM-1 (LLVLYFASSLIIPAIGMIIYFAR).

The invention includes in other aspects a method for preventing or treating a cancer by administering to a subject having a cancer the plasma membrane UCP inhibitor of the invention in effective amount to treat the cancer. Optionally an anti-tumor therapy may also be administered.

A method for regulating lysosomal pH, is provided according to another aspect of the invention. The method includes the step of modifying lysosomal UCP activity in a cell to regulate lysosomal pH. In some embodiments the cell is a T cell, a macrophage, or a neutrophil. The lysosomal UCP activity may be modified by contacting the cell with a lysosomal UCP inhibitor. In a preferred embodiment the lysosomal UCP inhibitor is selected from the group consisting of a dominant negative lysosomal UCP, and a lysosomal targeted binding peptide or molecule. The lysosomal UCP activity also may be modified by contacting the cell with a lysosomal UCP activator.

The invention in other aspects relates to a method for treating or preventing an infectious disease or a cancer by administering to a subject having or at risk of developing an infectious disease or a cancer a lysosomal UCP inhibitor in an effective amount for treating or preventing the infectious disease or cancer. In one embodiment the lysosomal UCP inhibitor is selected from the group consisting of a dominant negative lysosomal UCP, and a lysosomal targeted binding peptide or molecule. The method optionally includes the step of administering an antigen to the subject. In one embodiment the antigen is selected from the group consisting of a viral, a bacterial, a parasitic, and a fungal antigen. In another embodiment the subject is infected with an intracellular pathogen. Preferably the intracellular pathogen is an intracellular bacteria or an intracellular parasite.

According to another aspect of the invention a method for treating autoimmune disease is provided. The method involves administering to a subject having autoimmune disease a lysosomal UCP activator in an effective amount to prevent antigen presentation. In one embodiment the lysosomal UCP activator is a functional UCP or UCP fragment with a lysosomal membrane targeting molecule.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE SEQUENCES

SEQ ID NO: 1 is the nucleotide sequence of the human uncoupling (UCP-1) cDNA with GenBank Acc. no. U28480.
SEQ ID NO:2 is the predicted amino acid sequence of the translation product of human uncoupling cDNA (UCP-1).

SEQ ID NO:3 is the nucleotide sequence of the human uncoupling (UCP-2) cDNA with GenBank Acc. no. U82819.

SEQ ID NO:4 is the predicted amino acid sequence of the translation product of human uncoupling cDNA (UCP-2).

SEQ ID NO:5 is the nucleotide sequence of the human uncoupling (UCP-3S) cDNA with GenBank Acc. no. U82818.

SEQ ID NO:6 is the predicted amino acid sequence of the translation product of human uncoupling cDNA (UCP-3S).

DETAILED DESCRIPTION

The invention relates in some aspects to the finding that UCP is present in cellular membranes other than the mitochondrial membrane. For instance, UCP is expressed on the plasma membrane of rapidly dividing cells but not of growth arrested cells. This discovery has important implications for the regulation of cell death, division and differentiation.

In non-dividing cells of the body, mitochondria normally provide over 90% of cellular ATP (Rolfe, D. F. S. & Brown, G. C. *Cellular energy utilization and molecular origin of standard metabolic rate in mammals. Phys. Rev.* 77, 731-758 (1997)). Mitochondrial ATP synthesis is fueled by the oxidation of a variety of energy substrates (e.g., fatty acids, amino acids, and glucose), and it proceeds through the coupling of the electron transport chain to the activity of ATP synthase. Coincident to the transfer of electrons (or reducing equivalents) through components of the electron transport chain, protons are pumped into the intermembrane space, contributing to protonmotive force (Dp), across the inner membrane. Dp directly fuels mitochondrial ATP synthesis, as ATP synthase is driven by proton movement from the intermembrane space to the matrix. Uncoupling proteins (UCPs) present in the mitochondrial inner membrane have been proposed to cause mitochondrial proton leak and thereby reversibly uncouple oxidation from phosphorylation (Ricquier, D. & Bouillaud, F. *The uncoupling protein homologues: UCP1, UCP2, UCP3, StUCP,* and *AtUCP. Biochem. J.* 345, 161-179 (2000)).

Previously, it has been shown in co-pending U.S. patent application. Ser. No. 09/277,575 (and in the Examples section below) that UCP is expressed in the mitochondria of growth arrested and chemotherapy resistant cells but not in rapidly dividing cells. In these studies, we compared characteristics of mitochondrial metabolism in wild type and drug-resistant cells, which die apoptotically and non-apoptotically, respectively (Bhushan, A. et al. *Drug resistance results in alterations in expression of immune recognition molecules and failure to express Fas (CD95). Immunol. Cell Biol.* 76, 350-356 (1998)). Representative cell lines stained with the mitochondrial dyes Mitotracker Green, which quantitates mitochondria, and CmCX Ros Mitotracker Red (Molecular Probes, Eugene, Oreg.), which reflects mitochondrial membrane potential, revealed that the apoptotic resistant cells consistently have lower mitochondrial membrane potential as measured by the fluorescence uptake of the Mitotracker Red dye. In order to quantitate and confirm these results, we conducted a full analysis of the overall metabolic kinetics of oxidative phosphorylation, using L1210 and L1210/DDP cells as models of apoptotic sufficient and apoptotic resistance, respectively. Leak dependent oxygen consumption for a given value of mitochondrial membrane potential (e.g., between 145 and 150 mV) was found to be markedly higher in the L1210/DDP cells than in the wild type cells. Thus leak is increased in the resistant cell type. The overall kinetics of substrate oxidation and of phosphorylation were quite different between cell types and were consistent with the results of the cell staining studies described above. Moreover, in flow cytometric experiments using Mitotracker Red dyes and single cell analysis, L1210, HL60, and U937 cells consistently demonstrated a higher membrane potential than in their respective drug resistant counterparts. In general these data demonstrate that mitochondrial uncoupling proteins may serve dual functions, i.e., to change carbon sources for fuel and to protect the cells from damage from reactive oxygen species.

It was then discovered according to the invention that UCP is also expressed on other cellular membranes including the plasma membrane and the lysosome. It was further discovered that the expression and activity of UCP in each of these distinct locations has an important impact on the regulation of cellular growth and death. The metabolic shift from mitochondrial ATP production to cytosolic, glycolytic, and plasma ATP synthesis likely occurs as a mechanism to protect newly synthesized and exposed DNA that could be damaged by products of mitochondrial oxygen consumption. Thus regulation of UCP expression and activity protects cells from DNA damaging agents, including radiation and/or chemotherapy. Additionally, lysosomal UCP expression is characteristic of rapid cellular growth.

These findings of the invention have important implications in the treatment of disease and the study of cellular growth, death and differentiation, because it was not previously recognized that UCP was expressed in the plasma and lysosomal membranes and that plasma and lysosomal membrane UCP was involved in regulating various cellular functions.

Based on all these discoveries the invention includes in some aspects methods for increasing or decreasing the plasma membrane potential in a mammalian cell. The ability to manipulate the plasma membrane potential of a cell provides the ability to control the fate of the cell. When the plasma membrane potential of a cell is increased in a cell by increasing expression of UCP in the plasma membrane, the cell is able to respond to a signal by rapid cell division or cell death depending on the signal. If the plasma membrane potential of a cell is decreased, however, by inhibiting plasma membrane UCP activity, the cell is growth arrested and does not respond to the same signals. When the lysosomal membrane potential of a cell, however, is increased by increasing expression of UCP in the lysosomal membrane, the cell is growth arrested and respiratory burst is inhibited. If the lysosomal membrane potential of a cell is decreased by inhibiting lysosomal membrane UCP activity, the cell is able to respond to a signal by rapid cell division or cell death depending on the signal and respiratory burst is promoted. The invention encompasses mechanisms for controlling these complex interactions to regulate the processes of cellular death and division and for responding to microorganisms.

The methods of the invention have broad utility in regulating mammalian cell growth and death in vitro, in vivo and ex vivo. Because mammalian cells utilize the membrane potential and plasma and lysosomal membrane UCP in regulating their own growth and differentiation, any type of mammalian cell can be manipulated according to the methods of the invention.

The in vitro methods of the invention are useful for a variety of purposes. For instance, the methods of the invention may be useful for identifying drugs which have an effect, such as a preventative effect, on cellular division or death by contacting cells which are caused by the manipulations of the invention to undergo cellular division or death.

In addition to the in vitro methods, the methods of the invention may be performed in vivo or ex vivo in a subject to manipulate one or more cell types within the subject. An "ex vivo" method as used herein is a method which involves isolation of a cell from a subject, manipulation of the cell outside of the body, and reimplantation of the manipulated cell into the subject. The ex vivo procedure may be used on autologous or heterologous cells, but is preferably used on autologous cells. In preferred embodiments, the ex vivo method is performed on cells that are isolated from bodily fluids such as peripheral blood or bone marrow, but may be isolated from any source of cells. When returned to the subject, the manipulated cell will be programmed for cell death or division, depending on the treatment to which it was exposed. Ex vivo manipulation of cells has been described in several references in the art, including Engleman, E. G., 1997, *Cytotechnology*, 25:1; Van Schooten, W., et al., 1997, *Molecular Medicine Today*, June, 255; Steinman, R. M., 1996, *Experimental Hematology*, 24, 849; and Gluckman, J. C., 1997, *Cytokines, Cellular and Molecular Therapy*, 3:187. The ex vivo activation of cells of the invention may be performed by routine ex vivo manipulation steps known in the art. In vivo methods are also well known in the art. The invention thus is useful for therapeutic purposes and also is useful for research purposes such as testing in animal or in vitro models of medical, physiological or metabolic pathways or conditions.

A subject as used herein means a human or non-human mammal, including but not limited to, a dog, cat, horse, cow, pig, sheep, goat, chicken, primate, rat, and mouse.

In one aspect the invention is a method for inhibiting plasma membrane UCP expression in a rapidly dividing cell. The method is accomplished by contacting a rapidly dividing cell with a plasma membrane targeted UCP inhibitor to inhibit plasma membrane UCP expression. As discussed above, rapidly dividing cells express cell surface UCP but not (or low levels of) mitochondrial or lysosomal UCP. Although the invention is not limited to a particular mechanism, it is believed that rapidly dividing cells can process energy in the plasma membrane by converting energy sources such as glucose to heat that is released. When the plasma membrane UCP is inhibited according to the invention, the cell is unable to process the energy. Since there is no (or little) mitochondrial UCP present in these cells, the cells can no longer process the energy source and stop dividing, and eventually die.

A "rapidly dividing cell" as used herein is a cell which is undergoing mitotic growth. Such cells are well known in the art and include but are not limited to tumor cells, lymphocytes (T/B cells), bacteria, and pancreatic β cells.

In some embodiments of the invention the rapidly dividing cell is a tumor cell. The method is useful for inducing cell death in many types of mammalian cells but is particularly useful for inducing cell death in a tumor cell. A "tumor cell" as used herein is a cell which is undergoing unwanted mitotic proliferation. A tumor cell when used in the in vitro aspects of the invention can be isolated from a tumor within a subject or may be part of an established cell line. A tumor cell in a subject may be part of any type of cancer. Cancers include but are not limited to biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma [teratomas, choriocarcinomas]), stromal tumors and germ cell tumors; thyroid cancer, including thyroid adenocarcinoma and medullar carcinoma; and renal cancer including adenocarcinoma and Wilms tumor.

As used herein the term "cell death" is used to refer to either of the processes of apoptosis or cell lysis. In both apoptosis and cell lysis the cell dies but the processes occur through different mechanisms and when the cell is in a different metabolic state. Apoptosis is a process of cell death in which the cell undergoes shrinkage and fragmentation, followed by phagocytosis of the cell fragments. Apoptosis is well known in the art and can be assessed by any art recognized method. For example apoptosis is easily determined using flow cytometry, which distinguishes between live and dead cells. Flow cytometry is described in more detail in the Examples below.

Diabetes mellitus, which encompasses both Type I (i.e., Insulin Dependent Diabetes Mellitus (IDDM)) and Type II (i.e., Non-Insulin Dependent Diabetes Mellitus (NIDDM)), is known to affect more than one hundred million individuals worldwide. Although the exact cause of diabetes is unclear it is believed that diabetes may arise from any of a variety of physiological conditions such as genetic syndromes, viral infections, age related deterioration of structures responsible for maintaining the glycemic response, pancreatic disease, hormonal abnormalities, certain drugs or chemicals, insulin receptor abnormalities, etc. A "type I diabetic" is a subject who has diabetes mellitus caused by a destruction of beta cells in the pancreas. Type I diabetics require daily insulin administration which may be reduced but not altogether eliminated by careful restriction of diet.

Neither the genetic/environmental influences nor the inherent β cell characteristics that trigger immune-mediated destruction are completely understood. However, two features that are pivotal in susceptibility to β cell destruction are the expression of the cell surface molecule Fas and the metabolic state of the β cells. Fas can induce mitosis or apoptosis depending on the cell and the experimental circumstances. During the prediabetic stage of Type 1 diabetes, a β cell compensatory hypersecretion of insulin occurs and this process is accompanied by cell surface expression of the molecule Fas. When NOD mice, an animal model for Type 1 diabetes, are crossed with mice having the lpr mutation (Fas deficient), the animals are resistant to disease. In addition, destruction of β cells in the NOD accelerates when Fas Ligand is placed on the insulin promotor.

It has been discovered according to the invention that changes in cell surface expression of UCP contribute to β cell destruction or survival. β cell glucose-induced insulin secretion depends on increased intracellular ATP. The mitochondrial synthesis of ATP occurs through coupling of electron transport-dependent oxido-reductive reactions to ATP synthetase (oxidative phosphorylation). During this process, a proton gradient is generated by the pumping of protons out of the mitochondria increasing mitochondrial membrane potential. UCPs reversibly uncouple oxidative phosphorylation from electron transport decreasing mitochondrial membrane potential. Normal pancreatic β cells are in an uncoupled state and do not express Fas or UCP on their cell surface. As diabetes progresses to a first stage in which the patient is sick but before the pancreatic β cell are destroyed, it is believed that the patients pancreatic β cells become coupled and express Fas and UCP on the cell surface. The disease then progresses to the stage when pancreatic β cells begin to be killed. Before the cells are killed the metabolic state changes again to uncoupled and Fas is still expressed on the surface. When the cell is in an uncoupled state and Fas is expressed on the cell surface the cell is killed as soon as Fas is engaged without the need for any other agents.

A "type II diabetic" is a subject who has diabetes mellitus caused by abnormal insulin secretion and/or resistance to insulin action in target tissues. The physiological problem which occurs in a Type II diabetic is very different than that which occurs in a type I diabetic. In type II diabetes the pancreatic β cells undergo excessive proliferation. It is desirable to inhibit proliferation of these cells.

One method according to the invention for inducing pancreatic β cell death in a Type II diabetic involves the step of contacting a pancreatic β cell of a Type II diabetic with an amount of a plasma membrane targeted UCP inhibitor in an amount effective to induce pancreatic β cell death.

Autoimmune disease is a class of diseases in which an individuals own antibodies react with host tissue or in which immune effector T cells are autoreactive to endogenous self peptides and cause destruction of tissue. It is well established that MHC class II alleles act as major genetic elements in susceptibility to a variety of autoimmune diseases. These include rheumatoid arthritis, celiac disease, pemphigus vulgaris, and the prototype for autoimmune disease, systemic lupus erythematosus (SLE). The invention includes a new method for determining an individuals susceptibility to developing autoimmune disease. As used herein susceptibility to autoimmune disease indicates a likelihood of at least greater than the average of developing autoimmune disease, and in some embodiments 10% greater.

The methods of the invention also include methods for treating a subject having autoimmune disease to reduce associated cell death. One method is based on the ability to selectively remove γδ T cells which specifically recognize MHC class II HLA-DR on the surface of a self cell. When the γδ T cells recognize a tissue having significant amounts of MHC class II HLA-DR these T cells become activated and proliferate in order to kill more of the recognized cells. The methods of treatment are based on the concept of eliminating the activated γδ T cells from the body. These cells can be removed by contacting a γδ T cell with an amount of a plasma membrane targeted UCP inhibitor in an amount effective to induce γδ T cell death. This selective killing of the γδ cells inhibits cell death associated with autoimmune disease.

The invention is also useful for treating other diseases associated with rapidly dividing cells, such as rheumatoid arthritis and scleroderma. Rheumatoid arthritis is associated in its early stages with the rapid division of synoviocytes. This process is referred to a pannus formation. The rapidly dividing cells produce a substance that kills osteocytes leading to the hardening of the tissue. The plasma membrane targeted UCP inhibitors can be used to inhibit the proliferation of the synoviocytes, thus preventing the hardening of the tissue. In a similar manner plasma membrane targeted UCP inhibitors which are administered to skin of scleroderma subjects or subjects at risk of developing scleroderma can stop the rapid proliferation of skin cells which leads to this disease.

The methods of the invention are also useful for inducing cell death in a rapidly dividing microorganism, such as a bacteria. Bacteria include both gram negative and gram positive bacteria. Such gram positive bacteria include, but are not limited to *Pasteurella* species, *Staphylococci* species, and *Streptococcus* species. Gram negative bacteria include, but are not limited to, *Escherichia coli, Pseudomonas* species, and *Salmonella* species. Specific examples of infectious bacteria include but are not limited to: *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*.

When plasma membrane UCP expression or function is inhibited in bacteria, the ability to rapidly divide is interrupted. It is believed that bacterial cell death is accomplished in a similar manner to tumor cells when the plasma membrane UCP is inhibited. The methods of the invention may also be combined with other anti-bacterial therapies and performed on other types of rapidly dividing microorganisms.

The methods of inhibiting cell division in a rapidly dividing cell are accomplished by contacting the cell with a plasma membrane targeted UCP inhibitor. A "plasma membrane targeted UCP inhibitor" as used herein is a molecule that inhibits the expression or activity of UCP in the plasma membrane. Plasma membrane targeted UCP inhibitors include, for example, but are not limited to UCP binding peptides such as anti-UCP antibodies, UCP anti-sense nucleic acids, UCP dominant-negative nucleic acids and nucleotide analogs in an amount effect to inhibit plasma membrane UCP function.

Plasma membrane targeted UCP inhibitors include, for instance, nucleotides and nucleotide (purine and pyrimidine) analogs which have been modified to include a plasma membrane targeting sequence or are membrane impermeable. Nucleotides and nucleotide analogs include but are not limited to guanosine diphosphate (GDP). Purine analogs include but are not limited to guanosine diphosphate, 8-oxo-Adenosine, 8-oxo-Guanosine, 8-fluoro-Adenosine, 8-fluoro-Guanosine, 8-methoxy-Adenosine, 8-methoxy-Guanosine, 8-aza-Adenosine and 8-aza-Guanosine, azacitidine, Fludarabine phosphate, 6-MP, 6-TG, azathiprine, allopurinol, acyclovir, gancylovir, deoxycoformycin, and arabinosyladienine (ara-A), guanosine diphosphate fucose, guanosine diphosphate-2-fluorofucose, guanosine diphosphate-.beta.L-2-aminofucose, guanosine diphosphate-D-arabinose and 2-aminoadenosine. Some examples of pyrimidine analogues are uracil, thymine, cytosine, 5-fluorouracil, 5-chlorouracil, 5-bromouracil, dihydrouracil, 5-methylcytosine, 5-propynylthymine, 5-propynyluracil and 5-propynylcytosine, 5-fluorocytosine, Floxuridine, uridine, thymine, 3'-azido-3'-deoxythymidine, 2-fluorodeoxycytidine, 3-fluoro-3'-deoxythymidine; 3'-dideoxycytidin-2'-ene; and 3'-deoxy-3'-deoxythymidin-2'-ene, cytosine arabinoside. Other such compounds are known to those of skill in the art.

5-FU (e.g., "FLUOROURACIL" by Roche Labs., a division of Hoffman-LaRoche, Inc., Nutley, N.J. 07110) is a cytotoxic fluoropyrimidine antimetabolic commonly used in the palliative management of carcinoma of the colon, rectum, breast, ovarian, cervix, bladder, stomach, liver and pancreas.

5-FU has been shown to have synergistic interaction with other antineoplastic agents, interferons, and irradiation and is thus commonly used in combination therapy. 5-Fluorouracil (5-FU) has been used continuously since its development in 1957 by Duusinski and Heidelberger (U.S. Pat. No. 2,802,005). 5-FU was originally designed to work as an inhibitor of thymidylate synthetase (TS). TS is the enzyme which converts deoxyuridine 5'-O-monophosphate (dUMP) to deoxythymidine 5'-O-monophosphate (dTMP). It was previously believed that 5-FU retards tumor expansion by causing thymidine pools to become depleted in rapidly proliferating tumor cells. It has been found according to the invention that 5-FU that is targeted to the cell membrane and prevented from entering the cell can function by inhibiting plasma membrane UCP.

Protocols for the administration of 5-FU for treatment of human cancer involve infusion of the drug for long periods of time. 5-FU that is taken up by the cell is rapidly metabolized and excreted with a half-life in vivo of about 18 minutes. The effectiveness of 5-FU is hampered by rapid metabolism and formation of 2-fluoro-.beta.-alanine (FBAL) which is neurotoxic and cardiotoxic. When 5-FU is used according to the invention it is either modified to prevent cell uptake or targeted to the plasma membrane so that it is delivered to the plasma membrane and is not taken up by the cell. Thus, use of 5-FU according to the methods of the invention avoids the metabolic breakdown into toxic compounds that causes the associated side effects.

Screening assays for determining the sensitivity of a cell to 5-fluorouracil and its analogs have been described. Such an assay is described in Anai H, Maehara Y, Kusumoto H, Kusumoto T, Sugimachi K, Oncology 1988; 45(3):144-7, "Sensitivity test for 5-fluorouracil and its analogues, 1-(2-tetrahydrofuryl)-5-fluorouracil, uracil/1-(2-tetrahydrofuryl)-5-fluorouracil (4:1) and 1-hexylcarbamoyl-5-fluorouracil, using the subrenal capsule assay" This paper describes the testing of the chemosensitivity of human neoplastic tissues using 5-fluorouracil (5-FU) and its analogues: 1-(2-tetrahydrofuryl)-5-FU (FT), uracil/FT (UFT) and 1-hexylcarbamoyl-5-FU (HCFU), and the in vivo subrenal capsule (SRC) assay. The relative variation of tumor size (delta TS/TSo) was calculated and the chemosensitivity was considered to be sensitive when delta TS/TSo in the treated group was decreased to below −10%. The results of the study suggest that the SRC assay is useful for predicting the effective drug among 5-FU and 5-FU analogues, for individual patients with cancer. These assays can also be used with the plasma membrane targeted or membrane impermeable forms of 5-FU to predict which analogs are useful.

Fludarabine phosphate (e.g., "FLUDARA" by Berlex Labs., Richmond, Calif. 94804) is a purine analog antimetabolic commonly used in the treatment of chronic lymphocytic leukemia (CLL). Floxuridine (e.g., "FUDR" by Roche Labs., a division of Hoffman-LaRoche, Inc., Nutley, N.J. 07110) is a cytotoxic drug commonly used in the palliative management of gastrointestinal adenocarcinoma metastatic to the liver and is also used for treating brain, breast, head and neck cancers with liver metastases. The plasma membrane targeted or membrane impermeable forms of FLUDARA are also useful for the treatment of these cancers.

Thus nucleotides and nucleotide analogs can be modified to produce plasma membrane targeted UCP inhibitors by attaching a plasma membrane targeting sequence to the nucleotide or nucleotide analog. This can be accomplished by linking the nucleotide analog to a cell surface targeting molecule. Several methods for linking molecules are described below and others are known in the art. The nucleotide or nucleotide analogs may also be modified such that it is membrane impermeable to prevent uptake of the nucleotide analog by the cell. By using compounds which are not taken up by a cell but simply act on the cell surface UCP many of the toxic side effects associated with some of these drugs are avoided. The compounds will not have an effect on cells that do not have UCP expressed in the plasma membrane, because they cannot access the intracellular UCP. Additionally, the compounds will not be metabolized within cells to produce toxic compounds.

Plasma membrane targeted UCP inhibitors also include UCP binding peptides or molecules. The binding peptides or molecules can be delivered directly to the cell to act on the plasma membrane UCP. As long as they are delivered by a mechanism which will not facilitate uptake of the molecule into the cell then the UCP binding peptide or molecule will be targeted to the plasma membrane UCP as opposed to the mitochondrial or lysosomal UCP. The UCP binding peptide or molecule may also be attached to a targeting molecule which targets the peptide or molecule to the cell of interest, as discussed in more detail below.

The UCP binding peptides and molecules of the invention can be identified using routine assays, such as the binding and activation assays described in the Examples and elsewhere throughout this patent application.

The UCP binding molecule is an isolated molecule. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation, the molecular species may comprise only a small percentage by weight of the preparation. The molecular species is nonetheless substantially pure in that it has been substantially separated from the substances with which it may be associated in living systems.

The UCP binding molecules may be isolated from natural sources or synthesized or produced by recombinant means. Methods for preparing or identifying molecules which bind to a particular target are well-known in the art. Molecular imprinting, for instance, may be used for the de novo construction of macro molecular structures, such as peptides, which bind to a particular molecule. See for example, Kenneth J. Shea, *Molecular Imprinting of Synthetic Network Polymers*: The De novo Synthesis of Molecular Binding In Catalytic Sites, Trip, to May 1994; Klaus, Mosbach, Molecular Imprinting, Trends in *Biochem. Sci.,* 19(9), January 1994; and Wulff, G., In Polymeric Reagents and Catalysts (Ford, W. T., ed.) *ACS Symposium Series* No. 308, P. 186-230, *Am. Chem. Soc.* 1986. Binding peptides, such as antibodies, may easily be prepared by generating antibodies to UCP (or obtained from commercial sources) or by screening libraries to identify peptides or other compounds which bind to the UCP.

Many UCP antibodies are commercially available. These include but are not limited to those antibodies commercially available from Santa Cruz Biotechnology, Inc., e.g., UCP1 (m-17, sc-6529), UCP1 (C-17, sc-6528), UCP2 (A19, sc-6527), UCP2 (N19, sc-6526), UCP2 (c-20, sc-6525), and UCP3 (C-20, sc-7756); antibodies commercially available from Research Diagnostics Inc e.g., Goat anti-UCP1 HUMAN/Mouse/Rat (cat#RDI-UCP1Cabg); Goat anti- UCP1 HUMAN/Mouse/Rat (cat#RDI-MUCP1Cabg); Goat anti-UCP2 HUMAN/Mouse/Rat (cat#RDI-UCP2Nabg); Goat anti-UCP2 HUMAN/Mouse/Rat (cat#RDI-UCP2Cabg); Goat anti-UCP2 HUMAN/Mouse/Rat (cat#RDI-UCP2C1abg); Rabbit anti-Murine UCP1 (cat#RDI-MUCP12abrX); Rabbit anti-Murine UCP1 (cat#RDI-MUCP19abrX); Rabbit anti-Murine UCP2 (cat#RDI-MUCP2abrX); Rabbit anti-Murine UCP2 (cat#RDI-MUCP2CabrX); Rabbit anti-human UCP2 (cat#RDI-UCP2MabrX); UCP3L (see Boss, O et al (1997) FEBS Lett 408,38-42; Vidal-Plug A et al (1997) BBRC 235, 79-82); Rabbit anti-HUMAN UCP3 (cat#RDI-UCP3abrX); Rabbit anti-HUMAN UCP3 (cat#RDI-UCP3CbrX); Rabbit anti-HUMAN UCP3 (cat#RDI-UCP3MabrX); Rabbit anti-Rat UCP3 (cat#RDI-RTUCP3MabrX), etc.

Mimics of known binding molecules may also be prepared by known methods, such as (i) polymerization of functional monomers around a known binding molecule or the binding region of an antibody which also binds to the target (the template) that exhibits the desired activity; (ii) removal of the template molecule; and then (iii) polymerization of a second class of monomers in the void left by the template, to provide a new molecule which exhibits one or more desired properties which are similar to that of the template. The method is useful for preparing peptides, and other binding molecules which have the same function as binding peptides, such as polysaccharides, nucleotides, nucleoproteins, lipoproteins, carbohydrates, glycoproteins, steroids, lipids and other biologically-active material can also be prepared. Thus a template, such as a UCP binding antibody can be used to identify UCP inhibitors. It is now routine to produce large numbers of inhibitors based on one or a few peptide sequences or sequence motifs. (See, e.g., Bromme, et al., *Biochem. J.* 315:85-89 (1996); Palmer, et al., *J. Med. Chem.* 38:3193-3196 (1995)). For example, if UCP is known to interact with protein X at position Y, an inhibitor of UCP may be chosen or designed as a polypeptide or modified polypeptide having the same sequence as protein X, or structural similarity to the sequence of protein X, in the region adjacent to position Y. In fact, the region adjacent to the cleavage site Y spanning residues removed by 10 residues or, more preferably 5 residues, N-terminal and C-terminal of position Y, may be defined as a "preferred protein X site" for the choice or design of UCP inhibitors. Thus, a plurality of UCP inhibitors chosen or designed to span the preferred protein X binding site around position Y, may be produced, tested for inhibitory activity, and sequentially modified to optimize or alter activity, stability, and/or specificity.

The method is useful for designing a wide variety of biological mimics that are more stable than the natural counterpart, because they are typically prepared by the free radical polymerization of functional monomers, resulting in a compound with a non-biodegradable backbone. Thus, the created molecules would have the same binding properties as the UCP antibody but be more stable in vivo, thus preventing UCP from interacting with components normally available in its native environment. Other methods for designing such molecules include, for example, drug design based on structure activity relationships which require the synthesis and evaluation of a number of compounds and molecular modeling.

Binding molecules may also be identified by conventional screening methods, such as phage display procedures (e.g. methods described in Hart et al., *J. Biol. Chem.* 269:12468 (1994)). Hart et al. report a filamentous phage display library for identifying novel peptide ligands. In general, phage display libraries using, e.g., M13 or fd phage, are prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding.

Alternatively, UCP binding molecules can be identified from combinatorial libraries. Many types of combinatorial libraries have been described. For instance, U.S. Pat. Nos. 5,712,171 (which describes methods for constructing arrays of synthetic molecular constructs by forming a plurality of molecular constructs having the scaffold backbone of the chemical molecule and modifying at least one location on the molecule in a logically-ordered array); 5, 962, 412 (which describes methods for making polymers having specific physiochemical properties); and 5, 962, 736 (which describes specific arrayed compounds).

To determine whether a molecule binds to the appropriate target any known binding assay may be employed. For example, in the case of a peptide that binds to the plasma membrane UCP the molecule may be immobilized on a surface and then contacted with a labeled plasma membrane UCP (or vice versa). The amount of plasma membrane UCP which interacts with the molecule or the amount which does not bind to the molecule may then be quantitated to determine whether the molecule binds to plasma membrane UCP. A surface having a known molecule that binds to plasma membrane UCP such as a commercially available monoclonal antibody immobilized thereto may serve as a positive control. Several types of commercially available antibodies are described above.

Screening of molecules of the invention, also can be carried out utilizing a competition assay. If the molecule being tested competes with the known monoclonal antibody, as shown by a decrease in binding of the known monoclonal antibody, then it is likely that the molecule and the known monoclonal antibody bind to the same, or a closely related, epitope. Still another way to determine whether a molecule has the specificity of the known monoclonal antibody is to pre-incubate the known monoclonal antibody with the target with which it is normally reactive, and then add the molecule being tested to determine if the molecule being tested is inhibited in its ability to bind the target. If the molecule being tested is inhibited then, in all likelihood, it has the same, or a functionally equivalent, epitope and specificity as the known monoclonal antibody.

By using the known UCP (and other target) monoclonal antibodies of the invention, it is also possible to produce anti-idiotypic antibodies which can be used to screen other antibodies to identify whether the antibody has the same binding specificity as the known monoclonal antibody. Such anti-idiotypic antibodies can be produced using well-known hybridoma techniques (Kohler and Milstein, *Nature,* 256: 495, 1975). An anti-idiotypic antibody is an antibody which recognizes unique determinants present on the known monoclonal antibodies. These determinants are located in the hypervariable region of the antibody. It is this region which binds to a given epitope and, thus, is responsible for the specificity of the antibody. An anti-idiotypic antibody can be prepared by immunizing an animal with the known monoclonal antibodies. The immunized animal will recognize and respond to the idiotypic determinants of the immunizing known monoclonal antibodies and produce an antibody to these idiotypic determinants. By using the anti-idiotypic antibodies of the immunized animal, which are specific for the known monoclonal antibodies of the invention, it is possible to identify other clones with the same idiotype as the known monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody.

In one embodiment the binding peptides useful according to the invention are antibodies or functionally active antibody fragments. Antibodies are well known to those of ordinary skill in the science of immunology. Many of the binding peptides described herein are available from commercial sources as intact functional antibodies, as described above. As used herein, the term "antibody" means not only intact antibody molecules but also fragments of antibody molecules retaining specific binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983)).

As is well-known in the art, the complementarity determining regions (CDRS) of an antibody are the portions of the antibody which are largely responsible for antibody specificity. The CDR's directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody which is involved in the interaction with the antigen. The CDRs, and in particular the CDR3 regions, and more particularly the heavy chain CDR3 contribute to antibody specificity. Because these CDR regions and in particular the CDR3 region confer antigen specificity on the antibody these regions may be incorporated into other antibodies or peptides to confer the identical specificity onto that antibody or peptide.

According to one embodiment, the peptide of the invention is an intact soluble monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. As used herein the term "monoclonal antibody" refers to a homogenous population of immunoglobulins which specifically bind to an epitope (i.e. antigenic determinant), e.g., of plasma membrane UCP, lysosomal UCP etc.

The peptide useful according to the methods of the present invention may be an intact humanized a monoclonal antibody. A "humanized monoclonal antibody" as used herein is a human monoclonal antibody or functionally active fragment thereof having human constant regions and a binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.). For instance, a humanized form of the Pharmingen anti-Fas antibody used in the attached Examples could be easily prepared and used according to the methods of the invention.

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.*, 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA*, 90: 2551 (1993), Jakobovits et al., *Nature*, 362: 255-258 (1993), Bruggermann et al., *Year in Immuno.*, 7:33 (1993) and U.S. Pat. No. 5,569,825 issued to Lonberg).

The binding peptides may also be functionally active antibody fragments. Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology, 7th Ed., Blackwell Scientific Publications, Oxford*). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are used consistently with their standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

In addition to the binding peptides and molecules, the invention also encompasses the use of antisense oligonucleotides that selectively bind to a plasma membrane UCP nucleic acid molecule, and dominant negative UCP to reduce the expression of plasma membrane UCP. Antisense oligonucleotides are useful, for example, for inhibiting plasma membrane UCP in a cell in which it is ordinarily expressed in the plasma membrane.

As used herein, the term "antisense oligonucleotide" or "antisense" describes an oligonucleotide which hybridizes under physiological conditions to DNA comprising a particular gene or to an RNA transcript of that gene and, thereby, inhibits the transcription of that gene and/or the translation of the mRNA. The antisense molecules are designed so as to hybridize with the target gene or target gene product and thereby, interfere with transcription or translation of the target mammalian cell gene. Those skilled in the art will recognize that the exact length of the antisense oligonucleotide and its degree of complementarity with its target will depend upon the specific target selected, including the sequence of the target and the particular bases which comprise that sequence. The antisense must be a unique fragment. A unique fragment is one that is a 'signature' for the larger nucleic acid. It, for example, is long enough to assure that its precise sequence is not found in molecules outside of the UCP gene. As will be recognized by those skilled in the art, the size of the unique fragment will depend upon its conservancy in the genetic code. Thus, some regions of SEQ ID NO:1, 3, and 5, will require longer segments to be unique while others will require only short segments, typically between 12 and 32 base pairs (e.g. 12, 13, 14, 15, 16, 17, 18, 19, 20, 21, 22, 23, 24, 25, 26, 27, 28, 29, 30, 31 and 32 bases long).

It is preferred that the antisense oligonucleotide be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 and, more preferably, at least 15 consecutive bases which are complementary to the target. Most preferably, the antisense oligonucleotides comprise a complementary sequence of 20-30 bases. Although oligonucleotides may be chosen which are antisense to any region of the gene or RNA (e.g., mRNA) transcripts, in preferred embodiments the antisense oligonucleotides are complementary to 5' sites, such as translation initiation, transcription initiation or promoter sites, that are upstream of the gene that is targeted for inhibition by the antisense oligonucleotides. In addition, 3'-untranslated regions may be targeted. Furthermore, 5' or 3' enhancers may be targeted. Targeting to mRNA splice sites has also been used in the art but may be less preferred if alternative mRNA splicing occurs. In at least some embodiments, the antisense is targeted, preferably, to sites in which mRNA secondary structure is not expected (see, e.g., Sainio et al., *Cell Mol. Neurobiol.*, (1994) 14(5):439-457) and at which proteins are not expected to bind. The selective binding of the antisense oligonucleotide to a mammalian target cell nucleic acid effectively decreases or eliminates the transcription or translation of the mammalian target cell nucleic acid molecule. Reduction in transcription or translation of the nucleic acid molecule is desirable in preparing an animal model for further defining the role played by the mammalian target cell nucleic acid in modulating an adverse medical condition.

The invention also includes the use of a "dominant negative plasma membrane UCP" polypeptide. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide as used herein in a cell is a reduction in plasma membrane expressed UCP. One of ordinary skill in the art can assess the potential for a dominant negative variant of a protein, and using standard mutagenesis techniques to create one or more dominant negative variant polypeptides. For example, one of ordinary skill in the art can modify the sequence of the plasma membrane UCP by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity, or simply for presence in the plasma membrane. Other similar methods for creating and testing dominant negative variants of a protein will be apparent to one of ordinary skill in the art.

In addition to the plasma membrane UCP inhibitors of the invention an additional method for inhibiting plasma membrane UCP involves transfection of a cell with a UCP2 expression vector. Transfection of cells with a UCP2 expression vector causes decreased expression and activity of plasma membrane UCP. Thus it is useful to transfect a rapidly dividing cell with a UCP2 expression vector in order to induce growth arrest of the cell.

Additionally a UCP nucleic acid can be delivered to a cell such that the UCP peptide will be expressed in the plasma membrane of the cell. The UCP expression vectors and other relevant expression vectors described herein can be prepared and inserted into cells using routine procedures known in the art. These procedures are set forth below in more detail. "UCP nucleic acid", as used herein, refers to a nucleic acid molecule which: (1) hybridizes under stringent conditions to a nucleic acid having the sequence of SEQ ID NO:1, 3, and 5 and (2) codes for a UCP polypeptide. The preferred UCP nucleic acid has the nucleic acid sequence of SEQ ID NO:1, 3, and 5 (the nucleic acids encoding the human UCP-1, UCP-2, and UCP-3 polypeptides respectively). The UCP nucleic acids may be intact UCP nucleic acids which include the nucleic acid sequence of Sequence ID No.:1, 3, and 5 as well as homologs and alleles of a nucleic acid having the sequence of SEQ ID NO:1, 3, and 5. Intact UCP nucleic acids further embrace nucleic acid molecules which differ from the sequence of SEQ ID NO:1, 3, and 5 in codon sequence due to the degeneracy of the genetic code. The UCP nucleic acids of the invention may also be functionally equivalent variants, analogs and fragments of the foregoing nucleic acids. "Functionally equivalent", in reference to a UCP nucleic acid variant, analog or fragment, refers to a nucleic acid that codes for a UCP polypeptide that is capable of functioning as an UCP. The invention further embraces complements of the foregoing nucleic acids or of unique fragments of the foregoing nucleic acids. Such complements can be used, for example, as antisense nucleic acids for inhibiting the expression of UCP in a cell in order to create an experimental model of a cell in which UCP is not expressed.

The UCP nucleic acid molecules can be identified by conventional techniques, e.g., by identifying nucleic acid sequences which code for UCP polypeptides and which hybridize to a nucleic acid molecule having the sequence of SEQ ID NO:1, 3, and 5 under stringent conditions. The term "stringent conditions", as used herein, refers to parameters with which the art is familiar. More specifically, stringent conditions, as used herein, refer to hybridization at 65° C. in hybridization buffer (3.5×SSC, 0.02% Ficoll, 0.02% polyvinyl pyrolidone, 0.02% bovine serum albumin, 2.5 mM $NaH_2PO_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the UCP nucleic acid of the invention. The skilled artisan also is familiar with the methodology for screening cells and libraries for the expression of molecules, such as UCP, which can be isolated, followed by purification and sequencing of the pertinent nucleic acid molecule. In screening for UCP nucleic acid sequences, a Southern blot may be performed using the foregoing conditions, together with a radioactive probe. After washing the membrane to which the DNA is finally transferred, the membrane can be placed against x-ray film to detect the radioactive signal.

In general, homologs and alleles typically will share at least 40% nucleotide identity with SEQ ID NO:1, 3, and 5; in some instances, will share at least 50% nucleotide identity; and in still other instances, will share at least 60% nucleotide identity. The preferred homologs have at least 70% sequence homology to SEQ ID NO:1, 3, and 5. More preferably the preferred homologs have at least 80% and, most preferably, at least 90% sequence homology to SEQ ID NO:1, 3, and 5.

The invention also includes degenerate nucleic acids which include alternative codons to those present in the naturally occurring nucleic acid that codes for the human UCP polypeptide. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the naturally occurring nucleic acids in codon sequence due to the degeneracy of the genetic code.

The UCP nucleic acid, in one embodiment, is operably linked to a gene expression sequence which directs the expression of the UCP nucleic acid within a eukaryotic cell. The "gene expression sequence" is any regulatory nucleotide sequence, such as a promoter sequence or promoter-enhancer combination, which facilitates the efficient transcription and translation of the UCP nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, and β-actin. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined UCP nucleic acid. The gene expression sequences optionally include enhancer sequences or upstream activator sequences as desired.

Preferably, the UCP nucleic acid of the invention is linked to a gene expression sequence which permits expression of the UCP nucleic acid in the plasma membrane of a cell, e.g. a resistant tumor cell. A sequence which permits expression of the UCP nucleic acid in the plasma membrane of a tumor cell is one which is selectively active in the particular tumor cell and thereby causes the expression of the UCP nucleic acid in these cells. Those of ordinary skill in the art will be able to easily identify promoters that are capable of expressing a UCP nucleic acid in a tumor cell based on the type of tumor cell, as well as other known cells.

The UCP nucleic acid sequence and the gene expression sequence are said to be "operably linked" when they are covalently linked in such a way as to place the transcription and/or translation of the UCP coding sequence under the influence or control of the gene expression sequence. If it is desired that the UCP sequence be translated into a functional protein, two DNA sequences are said to be operably linked if induction of a promoter in the 5' gene expression sequence results in the transcription of the UCP sequence and if the nature of the linkage between the two DNA sequences does not (1) result in the introduction of a frame-shift mutation, (2) interfere with the ability of the promoter region to direct the transcription of the UCP sequence, or (3) interfere with the ability of the corresponding RNA transcript to be translated into a protein. Thus, a gene expression sequence would be operably linked to a UCP nucleic acid sequence if the gene expression sequence were capable of effecting transcription of that UCP nucleic acid sequence such that the resulting transcript might be translated into the desired protein or polypeptide.

The invention also encompasses methods for inducing cellular division in a growth arrested cell by expressing an UCP in a plasma membrane of a growth arrested cell under conditions in which the presence of the UCP within the plasma membrane of the growth arrested cell causes cell division of the growth arrested cell.

There are many ways to induce expression of UCP in a plasma membrane of a cell. For instance, it is possible to insert an intact UCP, or functional fragment thereof, into a plasma membrane using delivery vehicles such as liposomes. UCP is a naturally occurring plasma membrane protein having several transmembrane spanning regions including many hydrophobic residues. Proteins of this type can spontaneously insert into a biological membrane in an aqueous environment. See, e.g., U.S. Pat. No. 5,739,273 (which is hereby incorporated by reference) describing properties of bacteriorhodopsin C helix, a transmembrane spanning protein. The UCP can be inserted in to a biological membrane consistent with the methods described in U.S. Pat. No. 5,739,273 for inserting bacteriorhodopsin C into a membrane, including in lipid vesicles and by modification of various residues to increase the hydrophobicity of the molecule, without altering the function. Additionally UCP can be conjugated to a molecule which will insert in the membrane, causing the UCP to also insert in the membrane.

As set forth in U.S. Pat. No. 5,739,273 cell membranes are composed mainly of phospholipids and proteins, both containing hydrophobic and hydrophilic groups. The lipids orient themselves into an orderly bilayer configuration within the membrane core with the hydrophobic chains facing toward the center of the membrane while the hydrophilic portions are oriented toward the outer and inner membrane surfaces. The proteins are dispersed throughout the lipid layer, in some instances protruding through the surface of the membrane or extending from one side of the membrane to the other with some of the hydrophobic residues being buried in the interior of the lipid bilayer.

U.S. Pat. No. 5,739,273 teaches that a synthetic polypeptide maintaining the characteristics of a native polypeptide by including a hydrophobic alpha-helical transmembrane region containing one or more acidic or basic amino acids can be generated. Preferably, the amino acids are aspartic acid, glutamic acid, lysine, arginine or histidine. This is based on the teachings of Popot and Engelman, *Biochem.* 29:4031-4037 (1990), that recently proposed a two-stage model of helix formation for transmembrane proteins in which the alpha-helices first insert into the lipid bilayer and then assemble into a tertiary structure that includes interactions with other intramembrane alpha-helices of the protein or with alpha-helices of other polypeptides in the membrane.

The UCP insertion into the membrane can be enhanced using lipid vesicles. Lipid vesicles such as micelles can be formed by the addition of phospholipids to achieve a specific ratio of protein to phospholipid. The orientation of the chimeric protein components of the micelles can be controlled also, so that the micelles have an outer surface which is predominantly composed of the phospholipid moieties or predominantly composed of the protein moieties. The size of the micelles may also be controlled by varying the detergent employed, the nature of the added phospholipid, or the phospholipid/protein ratio.

Generally, the size of liposomes directly affects the rate at which they are cleared from the bloodstream. For example, smaller liposomes and negatively charged liposomes appear to be more stable and accumulate in the spleen and liver. Thus, the micelles and liposomes can be tailored to remain in the bloodstream for a desired period and to be delivered to specific organs. For example, small micelles can be formed with an outer surface exhibiting a predominantly negative charge from the phosphoinositol moiety.

UCP proteins include the intact native UCP in an isolated form as well as functionally active fragments and variants thereof. The native UCP protein has an amino acid sequence as presented in SEQ ID NO:2.

The relationship between plasma membrane UCP and cell surface Fas expression is important to the methods of the invention. When UCP is expressed on the plasma membrane Fas is also expressed on the cell surface in the plasma membrane. When UCP is not expressed on the plasma membrane Fas generally is transported to intracellular stores. When UCP and Fas are on the surface, engagement of Fas sends a signal to the cell instructing the cell to undergo cellular division. If a chemotherapeutic agent is added then the signal is changed to a signal which instructs the cell to undergo apoptosis. When Fas and UCP are not expressed on the cell surface, the cell is growth arrested and the cell is resistant to chemotherapy if the cell is a tumor cell.

An "apoptotic chemotherapeutic agent" as used herein is a group of molecules which function by a variety of mechanisms to induce apoptosis in rapidly dividing cells. Apoptotic chemotherapeutic agents are a class of chemotherapeutic agents which are well known to those of skill in the art. Chemotherapeutic agents include those agents disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc (Health Professions Division), incorporated herein by reference. Suitable chemotherapeutic agents may have various mechanisms of action. The classes of suitable chemotherapeutic agents include (a) Alkylating Agents such as nitrogen mustard (e.g. mechlorethamine, cylophosphamide, ifosfamide, melphalan, chlorambucil), ethylenimines and methylmelamines (e.g. hexamethylmelamine, thiotepa, alkyl sulfonates (e.g. busulfan), nitrosoureas (e.g. carmustine which is also known as BCNU, lomustine which is also known as CCNU semustine which is also known as methyl-CCNU, chlorozoticin, streptozocin), and triazines (e.g. dicarbazine which is also known as DTIC); (b) Antimetabolites such as folic acid analogs (e.g. methotrexate), pyrimidine analogs (e.g. 5-fluorouracil floxuridine, cytarabine, and azauridine and its prodrug form azaribine), and purine analogs and related materials (e.g. 6-mercaptopurine, 6-thioguanine, pentostatin); (c) Natural Products such as the vinca alkaloids (e.g. vinblastine, Vincristine), epipodophylotoxins (e.g. etoposide, teniposide), antibiotics (e.g. dactinomycin which is also known as actinomycin-D, daunorubicin, doxorubicin, bleomycin, plicamycin, mitomycin, epirubicin, which is 4-epidoxorubicin, idarubicin which is 4-dimethoxydaunorubicin, and mitoxanthrone), enzymes (e.g. L-asparaginase), and biological response modifiers (e.g. Interferon alfa); (d) Miscellaneous Agents such as the platinum coordination complexes (e.g. cisplatin, carboplatin), substituted ureas (e.g. hydroxyurea), methylhydiazine derivatives (e.g. procarbazine), adreocortical suppressants (e.g. mitotane, aminoglutethimide) taxol; (e) Hormones and Antagonists such as adrenocorticosteroids (e.g. prednisone or the like), progestins (e.g. hydroxyprogesterone caproate, medroxyprogesterone acetate, megestrol acetate), estrogens (e.g. diethyestilbestrol, ethinyl estradiol, and the like), antiestrogens (e.g. tamoxifen), androgens (e.g. testosterone propionate, fluoxymesterone, and the like), antiandrogens (e.g. flutamide), and gonadotropin-releasing hormone analogs (e.g. leuprolide) and (F) DNA damaging compounds such as adriamycin.

Additionally, the plasma membrane targeted UCP inhibitor can be used in combination with other therapies, such as radiation therapy. When a combination of therapies are used the effective amount to achieve the desired result, inhibition of cell proliferation will be less. This may be advantageous because it will reduce or eliminate any side effects associated with high concentrations of the individual therapies. A particularly preferred combination therapy is a plasma membrane targeted UCP inhibitor and radiation therapy. It is believed that radiation also contributes to the inhibition of plasma membrane UCP. Radiation sensitive cells are those cells that express plasma membrane UCP and radioresistant cells do not express plasma membrane UCP. The invention also includes methods of treating radioresistant cells by inducing UCP expression in the plasma membrane of these cells as described below and treating them with radiation.

In addition to the methods of manipulating cells, the invention is also useful for screening cells such as tumor cells to determine if those cells are susceptible to cellular division or cellular death, alone or in conjunction with treatment with a chemotherapeutic agent or other cell signal and kits for performing these screening assays. The screening method can be accomplished by isolating a tumor cell from a subject and detecting the presence of a UCP molecule in the plasma membrane of the tumor cell. The presence of a plasma membrane UCP indicates the tumor cell is susceptible to treatment with a chemotherapeutic agent.

The screening methods are particularly useful for determining if a tumor is sensitive to a chemotherapeutic agent. A tumor, however, may initially be sensitive to a particular chemotherapeutic agent and then as the therapy progresses the tumor may become resistant to that chemotherapeutic agent. The methods of the invention can be used to prevent the tumor from becoming resistant to a chemotherapeutic agent during therapy. The method involves the steps of administering to a subject in need of such treatment a chemotherapeutic agent and a plasma membrane UCP activator in a combined amount effective to kill the tumor. The plasma membrane UCP activator causes the plasma membrane UCP to become or remain activated, preventing the cell from developing a chemotherapy resistant phenotype. As the cell is held in this coupled state Fas is expressed on the surface and the chemotherapeutic agent can stimulate Fas mediated apoptosis.

A plasma membrane UCP activator as used herein is compound that induces the uncoupling function of a UCP molecule that is already expressed in the plasma membrane or causes a functional UCP to be expressed or inserted into the plasma membrane. These compounds include but are not limited to glucose, structural analogs of glucose, inhibitors of nucleotides and nucleotide analogs, and omega 3 fatty acids.

The combined amount of UCP activator and apoptotic chemotherapeutic agent effective to inhibit growth of the tumor cell is that amount effective to induce apoptosis of the tumor cell when the plasma membrane potential is decreased (as a result of the activation of the UCP). An effective amount means that amount necessary to delay the onset of, inhibit the progression of, halt altogether the onset or progression of the particular condition being treated. In general, an effective amount for treating a tumor cell is that amount necessary to halt the proliferation of the cell. In one embodiment, the effective amount is that amount necessary to kill the cell. In general, an effective amount for treating cancer will be that amount necessary to favorably affect mammalian cancer cell proliferation in-situ. An effective mount of the plasma membrane UCP activator is that amount sufficient to render the cell sensitive to chemotherapy. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

In some cases the screening assay may indicate that the tumor is mostly resistant to a chemotherapeutic agent. Resistant tumors may also be treated by the methods of the invention. One aspect of the invention involves the discovery that resistant tumors cells have a plasma metabolic state in which electron transport is coupled from oxidative phosphorylation in the plasma membrane because of the absence of UCP. It was discovered according to the invention that by altering the metabolic state of the tumor cell and thereby causing electron transport to be coupled to oxidative phosphorylation in the plasma membrane it is possible to cause the resistant cell to revert such that it becomes sensitive to chemotherapy. The method is performed by expressing a UCP in the plasma membrane of the resistant tumor cell under conditions in which the presence of the UCP within the plasma membrane causes cell division of the tumor cell.

Other screening assays can be performed according to the invention to identify the presence of rapidly dividing cells in a subject. The assay can be performed by isolating a sample of cells from a subject; and, detecting the presence of a plasma membrane UCP molecule in the plasma membrane of the cell, wherein the presence of the plasma membrane UCP molecule is indicative of a rapidly dividing chemotherapy sensitive cell.

Optionally, a targeting mechanism can be used to target the UCP inhibitor or activator to a specific cell type. It is desirable in many instances to specifically target a cell type to increase the efficiency and specificity of administration of the plasma membrane UCP inhibitor or activator, thus avoiding the effects that damage or destroy unrelated cells. Thus, an efficient delivery system which would enable the delivery of such drugs specifically to target cells would increase the efficacy of treatment and reduce the associated "side effects" of such treatments.

Methods of targeting drugs and other compounds to target cells are well known in the art. One method of targeting involves antibody or receptor targeting. Receptor or antibody targeting involves linking the UCP inhibitor or activator to a ligand or an antibody which has an affinity for a receptor or cell surface molecule expressed on the desired target cell surface. Using this approach, the UCP inhibitor or activator is intended to adhere to the target cell following formation of a ligand-receptor or antibody-cell surface antigen complex on the cell surface. The type of receptor or antibody used to target the cell will depend on the specific cell type being targeted.

A target molecule may be attached by a peptide or other type of bond such as a sulfhydryl or disulfide bond. Targeting molecules are described, for instance in U.S. Pat. No. 5,849,718 as well as many other references.

In general the targeting moiety is coupled to the UCP inhibitor or activator. The molecules may be directly coupled to one another, such as by conjugation or may be indirectly coupled to one another where, for example, the targeting moiety is on the surface of a liposome and the UCP inhibitor or activator is contained within the liposome. If the molecules are linked to one another, then the targeting moiety is covalently or noncovalently bound to the UCP inhibitor or activator in a manner that preserves the targeting specificity of the targeting moiety. As used herein, "linked" or "linkage" means two entities are bound to one another by any physiochemical means. It is important that the linkage be of such a nature that it does not impair substantially the effectiveness of the UCP inhibitor or activator or the binding specificity of the targeting moiety. Keeping these parameters in mind, any linkage known to those of ordinary skill in the art may be employed, covalent or noncovalent. Such means and methods of linkage are well known to those of ordinary skill in the art.

Linkage according to the invention need not be direct linkage. The components of the compositions of the invention may be provided with functionalized groups to facilitate their linkage and/or linker groups may be interposed between the components of these compositions to facilitate their linkage. In addition, the components of the present invention may be synthesized in a single process, whereby the components could be regarded as one in the same entity. For example, a targeting moiety specific for a tumor cell could be synthesized together with the UCP inhibitor or activator. These and other modifications are intended to be embraced by the present invention.

Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers have two different reactive groups that allow sequential conjugation reaction. Various types of commercially available cross-linkers are reactive with one or more of the following groups: primary amines, secondary amines, sulfhydriles, carboxyls, carbonyls and carbohydrates.

Non-covalent methods of conjugation also may be used to join the targeting moiety and the UCP inhibitor or activator. Non-covalent conjugation may be accomplished by direct or indirect means including hydrophobic interaction, ionic interaction, intercalation, binding to major or minor grooves of a nucleic acid and other affinity interactions.

Covalent linkages may be noncleavable in physiological environments or cleavable in physiological environments, such as linkers containing disulfide bonds. Such molecules may resist degradation and/or may be subject to different intracellular transport mechanisms. One of ordinary skill in the art will be able to ascertain without undue experimentation the preferred bond for linking the targeting moiety and the UCP inhibitor or activator, based on the chemical properties of the molecules being linked and the preferred characteristics of the bond.

For indirect linkage, the targeting moiety may be part of a particle, such as a liposome, which targets the liposome to tissues expressing the tumor cell. The liposome, in turn, may contain the UCP inhibitor or activator. The manufacture of liposomes containing UCP inhibitor or activator is fully described in the literature. Many are based upon cholesteric molecules as starting ingredients and/or phospholipids. They may be synthetically derived or isolated from natural membrane components. Virtually any hydrophobic substance can be used, including cholesteric molecules, phospholipids and fatty acids preferably of medium chain length (12C-20C). Preferred are naturally occurring fatty acids of between 14 and 18 carbons in length. These molecules can be attached to the UCP inhibitor or activator of the invention, with the lipophilic anchor inserting into the membrane of a liposome and the UCP inhibitor or activator tethered on the surface of the liposome for targeting the liposome to the cell.

In some embodiments the UCP activators and inhibitors are targeted to the lysosome. Native UCP molecules include a lysosomal targeting sequence which likely plays a role in targeting the UCP to the lysosomal membrane under the appropriate cellular conditions. This sequence is a NCT motif. This same motif can be used to target activators and inhibitors to the lysosomal membrane. Once the UCP is in the lysosome, it can function to regulate pH. Numerous publications describe targeting of nucleic acids and peptides to lysosomal compartments within cells. See, for instance, Pauly, D., et al., *Gene Ther.*, 5 (4), 473-80 (1998); Gerlier, D., *Cell Biol. Int.*, 18 (5), 315-20 (1994); Gough, N. et al., *J. Cell Sci.*, 112 (PT23) 4257-4269 (1999); Calvo, P., et al., *J. Biol. Chem.*, 274 (18), 12780-9 (1999); Williams, M., and Fukuda, M., *J. Cell. Biol.*, 111 (3), 955-66, (1990); Matthews, P., et al., *J.*

*Cell Biol.,* 118 (5), 1027-40 (1992); Sandoval, I., et al., *J. Biol. Chem.,* 269 (9), 6622-31 (1994); Blagoveshchenskaya, A., et al., *J. Biol. Chem.,* 273 (5), 2729-37 (1998); and Peters, C., *EMBO J.,* 9 (11), 3497-506, (1990), the entire contents of which are hereby incorporated by reference.

Native UCP also contains a mitochondrial targeting domain. This motif is described in Schleiff and McBride is a three unit motif.

Plasma membrane targeting sequences include hydrophobic moieties and membrane attachment domains. Hydrophobic moieties are well known in the art. A "membrane attachment domain," as used herein, refers to a domain that spans the width of a cell/plasma membrane, or any part thereof, and that functions to attach a UCP inhibitor to a cell membrane. Membrane attachment domains useful in the invention are those domains that function to attach a UCP inhibitor to a plasma membrane of an eukaryotic cell or the outer membrane of a prokaryotic cell. One skilled in the art understands that an appropriate membrane attachment domain is selected based on the type of cell in which the membrane-bound fusion protein is to be expressed.

A variety of naturally occurring and synthetic membrane attachment domains derived from eukaryotic and prokaryotic cell surface proteins are useful in the invention. For use in higher eukaryotic cells such as mammalian cells, a membrane attachment domain can be, for example, the membrane-spanning region of an integral membrane protein such as a cell surface receptor or cell adhesion molecule. Membrane attachment domains useful in the invention can be derived, for example, from cell surface receptors including growth factor receptors such as platelet derived growth factor receptor, epidermal growth factor receptor or fibroblast growth factor receptor; hormone receptors; cytokine receptors and T cell receptor. Membrane attachment domains useful in the invention also can be derived from cell adhesion molecules such as cadherins, integrins, selectins and members of the immunoglobulin superfamily; as well as other integral membrane proteins such as CD antigens. The amino acid sequences of exemplary membrane attachment domains are described herein (see, also Pigott and Power, The adhesion Molecule Facts Book San Diego: Academic Press, Inc. (1993) and Barclay et al., The Leukocyte Antigen Facts Book San Diego: Academic Press, Inc. (1993), each of which is incorporated herein by reference). If desired, the fusion protein can include the cytosolic domain, or portion thereof, of the heterologous protein from which the membrane attachment domain is derived.

Type I membrane attachment domains are transmembrane sequences of about 25 hydrophobic amino acid residues usually followed by a cluster of basic amino acids. Amino acids that are usually excluded from such membrane attachment domains include Asn, Asp, Glu, Gln, His, Lys and Arg, although where the domains form a multimeric complex in the membrane, there can be charged residues present. The orientation of a type I membrane attachment domain is such that the amino-terminal portion is extracellular. Such type I membrane attachment domains can be derived, for example, from CD2, CD40 or the IL-4 receptor.

Type II membrane attachment domains are transmembrane domains useful in the invention. The orientation of a type II membrane attachment domain is such that the carboxy-terminal portion is extracellular. Examples of type II membrane attachment domains include the transmembrane domain of CD72.

A membrane attachment domain of the invention also can be a phosphatidylinositol-glycan (PI-G) anchor, which is attached to the carboxy-terminal residue of a protein. A PI-G anchor can be derived, for example, from human placental alkaline phosphatase (HPAP), and can function to anchor a fusion protein to the cell surface (see, for example, Whitehorn et al., Biotechnology 13:1215-1219 (1995), which is incorporated herein by reference). PI-G-anchored molecules have a signal sequence at their carboxy-terminus that is cleaved off and replaced by the PI-G anchor. The residues at the PI-G attachment site and immediately following are typically small amino acids such as Ala, Asn, Asp, Gly, Cys or Ser. After the attachment residue, there is a hydrophobic sequence of about 10 to 20 residues starting 7-10 residues after the attachment point. Such hydrophobic PI-G-signal sequences generally lack the basic charged residues found in type I membrane attachment domains.

Type III membrane attachment domains, or segments thereof, also can be useful in the invention. Such type III membrane attachment domains are derived from eukaryotic cell surface molecules that cross the lipid bilayer numerous times. A membrane attachment domain useful in the invention can be, for example, one or more transmembrane domains derived from MDR1, a G-protein linked receptor or a protein of the rhodopsin superfamily. Exemplary membrane attachment domains include but are not limited to P-Cadherin (FILPILGAVLALLLLLTLLALLLLV); CD2 (IYLIIGICGGGSLLMVFVALLVFYIT); CD40 (ALVVIPIIFGILFAILLVLVFI); Contactin (ISGATAGVPTLLLGLVLPAP); IL-4 receptor (LLLGVSVSCIVILAVCLLCYVSIT); Mannose receptor (VAGVVIIVILLILTGAGLAAYFFY); M-CSF receptor (FLFTPVVVACMSIMALLLLLLLLLL); PDGFR .beta. chain (VVVISAILALVVLTIISLIILIMLWQKKPR); PDGFR .alpha. chain (ELTVAAAVLVLLVIVSISLIVLVVTW); P-Selectin (LTYFGGAVASTIGLIMGGTLLALL); Rat Thy-1 (VKCGGISLLVQNTSWLLLLLLSLSFLQATDFISL); TNFR-1 (TVLLPLVIFFGLCLLSLLFIGLM); and VCAM-1 (LLVLYFASSLIIPAIGMIIYFAR).

The term "heterologous," as used herein in reference to a membrane attachment domain operatively fused to a UCP inhibitor, means a membrane attachment domain derived from a source other than the gene encoding the UCP inhibitor. A heterologous membrane attachment domain can be synthetic or can be encoded by a gene distinct from the gene encoding the UCP inhibitor to which it is fused.

The term "operatively fused," as used herein in reference to a UCP inhibitor and a heterologous membrane attachment domain, means that the UCP inhibitor and membrane attachment domain are fused in the correct reading frame such that, under appropriate conditions, a full-length fusion protein is expressed. One skilled in the art would recognize that such a fusion protein can comprise, for example, an amino-terminal UCP inhibitor operatively fused to a carboxyl-terminal heterologous membrane attachment domain or can comprise an amino-terminal heterologous membrane attachment domain operatively fused to a carboxyl-terminal UCP inhibitor.

The term "membrane-bound," as used herein in reference to a fusion protein means stably attached to a cellular membrane. The term "fusion protein," as used herein, means a hybrid protein including a synthetic or heterologous amino acid sequence.

The plasma membrane UCP inhibitor is delivered to the rapidly dividing cell in an amount effective to inhibit rapid mitotic growth. An effective amount to inhibit rapid mitotic growth is that amount which is sufficient to slow down, or inhibit altogether the proliferation and/or rapid mitotic growth of the rapidly dividing cell.

As used herein, the term "dissipation of cellular proton motor force" refers to the relative amount of protons in the cell. It can be assessed by measuring plasma, lysosomal, or mitochondrial membrane potential depending on the UCP being studied. As used herein "plasma membrane potential" is the pressure on the inside of the plasma membrane measured relative to the extracellular fluid which is created by the generation and dissipation of charge within the cell. The "lysosomal membrane potential" is the pressure on the inside of the lysosomal membrane measured relative to the cytoplasma which is created by the generation and dissipation of charge within the lysosome. The plasma or lysosomal membrane potential is maintained by the energy generating system of the plasma or lysosomal membrane respectively. In most tissues electron transport is coupled to oxidative phosphorylation resulting in the production of ATP from glucose. UCPs can cause the reversible uncoupling of electron transport and oxidative phosphorylation, which leads to a decrease in the mitochondrial membrane potential, or as discovered herein the plasma or lysosomal membrane potential. Other tissue, often referred to as the immuno-privileged tissue such as the brain, testis, ovary, eye, and pancreatic β cells, express UCPs which cause electron transport to be uncoupled to oxidative phosphorylation under normal conditions. In these tissues glucose cannot be converted to ATP while the UCP is active because of the uncoupling and the energy produced is converted into other energy forms such as heat and released. If the metabolic processing systems in these tissues are caused to undergo coupling the membrane potential would increase.

The absolute levels of the plasma membrane potential vary depending on the cell or tissue type. As used herein an "increase in plasma or lysosomal membrane potential" is an increase relative to the normal status of the cell being examined and results from the prevention of dissipation of proton motor force with respect to plasma or lysosomal respectively. "Prevention" as used herein refers to a decrease or reduction in the amount of dissipation that would ordinarily occur in the absence of the stimulus applied according to the methods of the invention to cause coupling. If electron transport and oxidative phosphorylation are normally uncoupled within the plasma or lysosomal membrane of the cell then the baseline potential will be relatively low and when the ATP generating systems are coupled an increase in plasma or lysosomal membrane potential from that baseline level is observed. Likewise, a "decrease in plasma or lysosomal membrane potential" is a decrease relative to the normal status of the cell being examined and results from the dissipation of proton motor force. If electron transport and oxidative phosphorylation are normally coupled within the cell then the baseline potential will be relatively high and when the ATP generating systems are uncoupled a decrease in plasma membrane potential from that baseline level is observed. Plasma or lysosomal membrane ATP synthase is likely the source of ATP for the plasma or lysosomal membrane UCP.

Changes in plasma or lysosomal membrane potential can be assessed by any method known in the art for making such measurements. For example the plasma or lysosomal membrane potential may be assessed using the well known comet assay, where whole cells are electrophoresed on an agarose gel and examined for the presence of a tail. Alternatively it may be measured using electrodes placed on opposite sides of the membrane. Plasma or lysosomal membrane potential may also be measured cytometrically by incubating cells for approximately 20 minutes at room temperature with a plasma or lysosomal membrane specific fluorescent probe. The aggregation state and consequently the fluorescence emission of fluorescent probe changes as the plasma or lysosomal membrane potential is altered. Flow cytometry permits the examination of more than one, for instance eight, fluorescent markers concurrently. This method is described in more detail in the Examples section below In addition to examining the plasma or lysosomal membrane potential, studies can be performed to determine the rate of glucose utilization and oxidation and measurements of proton leak can be assessed by a top-down elasticity analysis, each of which is described in more detail in the Examples below. An additional method for determining if a cell expresses active UCP in the plasma or lysosomal membrane is an adherence test. Wild type tumor cells that express active UCP in the cell membrane but not in the mitochondrial or lysosomal membranes are not adherent to tissue culture flasks having a negative charge but are adherent to poly-lysine which is positively charged. Cells which do not express UCP in the plasma membrane but do express mitochondrial or lysosomal UCP, such as melanoma cells, do not adhere to poly-lysine but adhere well to negatively charged tissue culture dishes. Thus the adherence assay can be used to detect the presence of active plasma membrane UCP or lysosomal UCP.

The invention also relates to the discovery that UCP is expressed in the lysosomal membrane. This finding has important implications for the regulation of many physiological processes including, antigen presentation, respiratory burst, cholesterol trafficking and inflammatory disease.

Antigen presentation is a complex process involving a pathway of intracellular trafficking and peptide loading of MHC class II molecules in the lysosome. Manipulation of elements involved in this pathway can result in regulation of immune system function. One important element in the lysosomal processing of antigen is pH. The lysosome must maintain an acidic pH in order to properly process antigen and ultimately present antigen in the context of MHC class II. It has been discovered that lysosomal pH can be manipulated by manipulating lysosomal UCP expression and activity. If active UCP is expressed in the lysosome protons are dissipated and the pH is altered, thus preventing antigen presentation. If the expression or activity of the UCP is inhibited the lysosome can develop an acidic pH to promote antigen presentation.

Thus the invention in some aspects relates to methods of inhibiting lysosomal UCP activity. It is particularly useful to inhibit lysosomal UCP for the prevention and treatment of infections. Thus, the invention relates to the prevention and treatment of infectious disease by inhibiting lysosomal UCP. Although not bound by any mechanism, Applicant believes that the inhibition of lysosomal UCP activity causes two physiological effects which leads to the prevention and treatment of infections. Firstly, the inhibition of lysosomal UCP promotes the development of an acidic intra-lysosomal environment, which promotes antigen presentation. When antigen presenting cells (APCs) are exposed to an antigen of an infectious organism under conditions in which lysosomal UCP activity is inhibited the antigen can be processed and presented on the cell surface. The immune system can then mount an effective antigen specific immune response against the antigen, thus providing the host with a prophylactic or therapeutic immune response.

Additionally, inhibition of lysosomal UCP can promote respiratory burst, which is useful for treating intracellular pathogens. Respiratory burst is a process in which cells, e.g., neutrophils, macrophage undergo a large burst in respiration and convert oxygen to toxic oxygen metabolites such as the superoxide anion. This class of metabolites, also referred to as reactive oxygen species (ROS) include but are not limited to hydrogen peroxide, superoxide anion, hypochlorous acid, peroxynitritesinglet oxygen, and hydroxyl radical. ROS are believed to damage microbes by reacting with proteins, nucleic acids, and membrane lipids, and preventing these molecules from functioning. These compounds are generated in large quantities during respiratory burst and function either intracellularly or are released into the extracellular space.

Thus, in one aspect, the present invention provides a method for preventing or treating an infectious disease or cancer in a subject having or at risk of developing an infectious disease or cancer by administering a lysosomal UCP inhibitor to a cell of the subject in an amount effective to prevent lysosomal UCP activity. A "lysosomal UCP inhibitor" is any molecular species that prevents UCP activity in the lysosome. The lysosomal UCP inhibitor may function by preventing the activity of an expressed UCP, preventing the transcription of a lysosomal UCP gene, preventing the processing or translation of a lysosomal UCP mRNA or preventing the processing, trafficking, or activity of a lysosomal UCP protein when administered in vivo or in vitro to a mammalian cell which is otherwise competent to express active lysosomal UCP. Thus, for example, lysosomal UCP inhibitors include lysosomal targeted nucleotides, nucleotide analogs, and binding peptides, repressors which prevent induction and/or transcription of the lysosomal UCP gene, antisense sequences which selectively bind to lysosomal UCP DNA or RNA sequences and which prevent the transcription or translation of the lysosomal UCP gene, competitive and non-competitive inhibitors of the activity of the lysosomal UCP protein. In some embodiments of the invention the lysosomal UCP inhibitor is a lysosomal UCP binding molecule or a lysosomal UCP antisense molecule. UCP binding proteins are those described above such as antibodies, including fragments of antibodies, such as Fc. These peptides are targeted to the lysosomal membranes in order to selectively bind to and inhibit the activity of lysosomal UCP. Other types of inhibitors include ribozymes which interfere with the transcription, processing, or translation of lysosomal UCP mRNA. In other embodiments the UCP inhibitor is a nucleotide or nucleotide analog targeted to the lysosome. These nucleotides and analogs are those described above, such as ATP.

Another preferred lysosomal UCP inhibitor is tunicamycin. Tunicamycin promotes intracellular trafficking of the lysosomal UCP from the intracellular location to the plasma membrane. When cells are administered tunicamycin the UCP is selectively targeted away from the lysosome, preventing respiratory burst and promoting antigen presentation. If tunicamycin therapy is combined with a plasma membrane targeted UCP inhibitor the cells are killed.

The terms "prevent" and "preventing" as used herein refer to inhibiting completely or partially the expression or activity of a UCP molecule, as well as inhibiting an increase in the expression or activity of a UCP molecule or inhibiting completely or partially antigen presentation or respiratory burst or inhibiting an increase in antigen presentation or respiratory burst.

Thus, in some aspects, the invention encompasses a method for stimulating an MHC class II immune response by administering to a cell a lysosomal UCP inhibitor in an amount effective to prevent lysosomal UCP activity. The method is performed in order to enhance antigenic peptide loading in MHC class II complexes, and for promoting specific antigen immune responses. Therefore, in one aspect, the present invention provides methods for promoting antigen-specific immune responses. The UCP inhibitor can be administered in conjunction with a specific antigen, such that that specific antigen is preferentially loaded into the MHC class II molecules. These methods are useful for both in vitro and in vivo antigen loading.

When used with mammalian cells in vitro, such methods have utility for loading of specific antigens within the MHC molecules. Cells with specific antigen loading in class II molecules have utility in a variety of analytical and diagnostic assays. These cells are also useful as therapeutic agents. For instance, the cells can be used in culture to study immune responses or to screen the effect of putative drugs on inhibiting or promoting antigen-specific immune responses. Additionally, the cells could be administered to a mammalian subject to promote an antigen-specific T cell response. When administered to a subject, the class II MHC/antigen complexes on the surface of the cell would interact with endogenous T cells, inducing an immune cascade, and thus producing an antigen-specific immune response. In preferred embodiments, the cells manipulated in vitro have been isolated from the same subject ex vivo.

The UCP inhibitors are also useful for treating a mammalian subject in vivo to induce an antigen-specific immune response. It is useful to produce antigen-specific immune responses against any foreign antigen whether it is capable of causing a pathological state or any damage to its mammalian host. The terms "foreign antigen" or "antigen" are used synonymously to refer to a molecule capable of provoking an immune response in a host, wherein the antigen is not a self-antigen, as defined above. Thus, the term antigen or foreign antigen specifically excludes self-antigens. Self-antigens are used herein to refer to the peptide-antigens of autoimmune disorders. An immune response against the self-antigen results in an autoimmune disorder. The term self-antigen does not include, however, antigens such as cancer antigens, which are recognized by the host as foreign and which are not associated with autoimmune disease. Thus, the term antigen specifically excludes self-antigens and broadly includes any type of molecule (e.g. associated with a host or foreign cell) which is recognized by a host immune system as being foreign. Antigens include, but are not limited to, cancer antigens and microbial antigens and may be composed of cells, cell extracts, polysaccharides, polysaccharide conjugates, lipids, glycolipids, carbohydrates, peptides, proteins, viruses, viral extracts, etc.

A "cancer antigen", as used herein, is a compound which is associated with a tumor or cancer cell surface and which is capable of provoking an immune response when expressed on the surface of an antigen-presenting cell in the context of a class II MHC molecule. Cancers or tumors include those described above.

Cancer antigens include but are not limited to Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-AL 11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1 and CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, Imp-1, EBV-encoded nuclear antigen (EBNA)-1, or c-erbB-2.

In some embodiments, cancers or tumors escaping immune recognition and tumor-antigens associated with such tumors (but not exclusively), include acute lymphoblastic leukemia (etv6; aml1; cyclophilin b), B cell lymphoma (Ig-idiotype), glioma (E-cadherin; α-catenin; β-catenin; γ-catenin; p120ctn), bladder cancer (p21ras), biliary cancer (p21 ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)—C017-1A/GA733; APC), choriocarcinoma (CEA), epithelial cell-cancer (cyclophilin b), gastric cancer (HER2/neu; c-erbB-2; ga733 glycoprotein), hepatocellular cancer (α-fetoprotein), hodgkins lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung carcinoma (HER2/neu; c-erbB-2), nasopharyngeal cancer (Imp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), squamous cell cancers of cervix and esophagus (viral products such as human papilloma virus proteins), testicular cancer (NY-ESO-1), T cell leukemia (HTLV-1 epitopes), and melanoma (Melan-A/MART-1; cdc27; MAGE-3; p21 ras; gp100$^{Pmel117}$). These antigens are also useful according to the invention.

For examples of tumor antigens which bind to either or both MHC class I and MHC class II molecules, see the following references: Coulie, *Stem Cells* 13:393-403, 1995; Traversari et al., *J. Exp. Med.* 176:1453-1457, 1992; Chaux et al., *J. Immunol.* 163:2928-2936, 1999; Fujie et al., *Int. J. Cancer* 80:169-172, 1999; Tanzarella et al., *Cancer Res.* 59:2668-2674, 1999; van der Bruggen et al., *Eur. J. Immunol.* 24:2134-2140, 1994; Chaux et al., *J. Exp. Med.* 189:767-778, 1999; Kawashima et al, *Hum. Immunol.* 59:1-14, 1998; Tahara et al., *Clin. Cancer Res.* 5:2236-2241, 1999; Gaugler et al., *J. Exp. Med.* 179:921-930, 1994; van der Bruggen et al., *Eur. J. Immunol.* 24:3038-3043, 1994; Tanaka et al., *Cancer Res.* 57:4465-4468, 1997; Oiso et al., *Int. J. Cancer* 81:387-394, 1999; Herman et al., *Immunogenetics* 43:377-383, 1996; Manici et al., *J. Exp. Med.* 189:871-876, 1999; Duffour et al., *Eur. J. Immunol.* 29:3329-3337, 1999; Zorn et al., *Eur. J. Immunol.* 29:602-607, 1999; Huang et al., *J. Immunol.* 162: 6849-6854, 1999; Boël et al., *Immunity* 2:167-175, 1995; Van den Eynde et al., *J. Exp. Med.* 182:689-698, 1995; De Backer et al., *Cancer Res.* 59:3157-3165, 1999; Jäger et al., *J. Exp. Med.* 187:265-270, 1998; Wang et al., *J. Immunol.* 161:3596-3606, 1998; Aarnoudse et al., *Int. J. Cancer* 82:442-448, 1999; Guilloux et al., *J. Exp. Med.* 183:1173-1183, 1996; Lupetti et al., *J. Exp. Med.* 188:1005-1016, 1998; Wölfel et al., *Eur. J. Immunol.* 24:759-764, 1994; Skipper et al., *J. Exp. Med.* 183:527-534, 1996; Kang et al., *J. Immunol.* 155:1343-1348, 1995; Morel et al., *Int. J. Cancer* 83:755-759, 1999; Brichard et al., *Eur. J. Immunol.* 26:224-230, 1996; Kittlesen et al., *J. Immunol.* 160:2099-2106, 1998; Kawakami et al., *J. Immunol.* 161:6985-6992, 1998; Topalian et al., *J. Exp. Med.* 183:1965-1971, 1996; Kobayashi et al., *Cancer Research* 58:296-301, 1998; Kawakami et al., *J. Immunol.* 154:3961-3968, 1995; Tsai et al., *J. Immunol.* 158:1796-1802, 1997; Cox et al., *Science* 264:716-719, 1994; Kawakami et al., *Proc. Natl. Acad. Sci. USA* 91:6458-6462, 1994; Skipper et al., *J. Immunol.* 157:5027-5033, 1996; Robbins et al., *J. Immunol.* 159:303-308, 1997; Castelli et al, *J. Immunol.* 162: 1739-1748, 1999; Kawakami et al., *J. Exp. Med.* 180:347-352, 1994; Castelli et al., *J. Exp. Med.* 181:363-368, 1995; Schneider et al., *Int. J. Cancer* 75:451-458, 1998; Wang et al., *J. Exp. Med.* 183:1131-1140, 1996; Wang et al., *J. Exp. Med.* 184:2207-2216, 1996; Parkhurst et al., *Cancer Research* 58:4895-4901, 1998; Tsang et al., *J. Natl Cancer Inst* 87:982-990, 1995; Correale et al., *J. Natl Cancer Inst* 89:293-300, 1997; Coulie et al., *Proc. Natl. Acad. Sci. USA* 92:7976-7980, 1995; Wölfel et al., *Science* 269:1281-1284, 1995; Robbins et al., *J. Exp. Med.* 183:1185-1192, 1996; Brandle et al., *J. Exp. Med.* 183:2501-2508, 1996; ten Bosch et al., *Blood* 88:3522-3527, 1996; Mandruzzato et al., *J. Exp. Med.* 186:785-793, 1997; Gueguen et al., *J. Immunol.* 160:6188-6194, 1998; Gjertsen et al., *Int. J. Cancer* 72:784-790, 1997; Gaudin et al., *J. Immunol.* 162:1730-1738, 1999; Chiari et al., *Cancer Res.* 59:5785-5792, 1999; Hogan et al., *Cancer Res.* 58:5144-5150, 1998; Pieper et al., *J. Exp. Med.* 189:757-765, 1999; Wang et al., *Science* 284:1351-1354, 1999; Fisk et al., *J. Exp. Med.* 181:2109-2117, 1995; Brossart et al., *Cancer Res.* 58:732-736, 1998; Röpke et al., *Proc. Natl. Acad. Sci. USA* 93:14704-14707, 1996; Ikeda et al., *Immunity* 6:199-208, 1997; Ronsin et al., *J. Immunol.* 163:483-490, 1999; Vonderheide et al., *Immunity* 10:673-679, 1999. These antigens as well as others are disclosed in PCT Application PCT/US98/18601.

In other aspects, the antigen is a microbial antigen and the methods of the invention are useful for treating or preventing infectious disease. An infectious disease, as used herein, is a disease arising from the presence of a foreign microorganism in the body. A microbial antigen, as used herein, is an antigen of a microorganism and, includes but it not limited to, infectious virus, infectious bacteria, and infectious fungi.

Examples of infectious virus include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious bacteria include but are not limited to: *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* such as *Plasmodium falciparum, Plasmodium malariae, Plasmodium ovale*, and *Plasmodium vivax* and *Toxoplasma gondii*.

The lysosomal UCP inhibitors are also useful for treating disorders susceptible to respiratory burst. Inhibition of lysosomal UCP allows cells to produce reactive oxygen species in order to kill intracellular pathogens. Thus, in some aspects the invention relates to a method of treating a subject infected with an intracellular pathogen. In one embodiment the lysosomal UCP inhibitor is tunicamycin.

Microorganisms can be classified based on whether they are intracellular or extracellular. An intracellular pathogen, as used herein, is a pathogen whose entire life cycle is intracellular or a pathogen which has an obligate intracellular existence at a critical stage in their life cycles. Examples of human intracellular parasites include *Leishmania* spp., *Plasmodium* spp., *Trypanosoma cruzi, Toxoplasma gondii, Babesia* spp., and *Trichinella spiralis*. Other intracellular pathogens such as bacteria are well known in the art. Parasites which are mainly extracellular but with an obligate intracellular existence at a critical stage in their life cycles are referred to herein as "obligate intracellular parasites". These parasites may exist most of their lives or only a small portion of their lives in an extracellular environment, but they all have at lest one obligate intracellular stage in their life cycles. This latter category of parasites includes *Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp. The methods of the invention are useful for treating infection resulting from both intracellular pathogens and obligate intracellular pathogens which have at least in one stage of their life cycle that is intracellular. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Activators of lysosomal UCP are useful for raising the lysosomal pH and preventing antigen presentation and respiratory burst as well as for preventing trafficking and preventing and treating inflammatory disease. When used in vivo, methods of the invention in some aspects are useful for treating or preventing disorders associated with a specific antigenic immune response. Thus, in some embodiments of the invention, the methods are used to treat mammals at risk of, or afflicted with, autoimmune disease. Autoimmune disease is a disorder in which the host's immune response is defective and results in the production of a specific immune response against the individual's own antigens or components. In an autoimmune disease, an individual's own antibodies react with host tissue or in which immune effector T cells are autoreactive to endogenous self peptides and cause destruction of tissue. It is well established that MHC class II alleles act as major genetic elements in susceptibility to a variety of autoimmune diseases. The structures recognized by T cells, the cells that cause autoimmunity, are complexes comprised of class II MHC molecules and antigenic peptides. When the T cells react with the host's class II MHC molecules-peptide complexes derived from a host's own gene products, autoimmune disease can result. If these class II MHC/peptide complexes are inhibited from being formed, the autoimmune response is reduced or suppressed, and thus is inhibited according to the invention. The peptide-antigen of autoimmune disorders are self-antigens. Any autoimmune disease in which class II MHC/peptide complexes play a role may be treated according to the methods of the present invention. Such autoimmune diseases include, but are not limited to, juvenile-onset diabetes (insulin-dependent), multiple sclerosis, pemphigus vulgaris, Graves disease, myasthenia gravis, systemic lupus erythematosus (SLE), celiac disease rheumatoid arthritis, and Hashimoto's thyroiditis.

The methods of the invention are also useful for treating mammals at risk of, or afflicted with, allergic responses. An "allergic response" as used herein is a disorder in which the host's immune response to a particular antigen is unnecessary or disproportionate, resulting in pathology. An allergic response may occur, in part, because a T cell recognizes a particular class II MHC/peptide complex and triggers a cascade of immune response. If the class II MHC/peptide complex is inhibited from being formed, the allergic response is reduced or suppressed. Any allergic response in which class II MHC/peptide complexes play a role may be treated according to the methods of the present invention. Allergies arising from an allergic response include, but are not limited to, allergies to pollen, ragweed, shellfish, domestic animals, (e.g., cats and dogs), B-venom, and the like. A subset of allergic responses produce asthma. Allergic asthmatic responses are also included within the definition of the term "allergic response". It is particularly desirable to treat severe or life-threatening allergic responses, such as those arising during asthmatic attacks or anaphylactic shock, according to the methods of the invention.

The methods of the invention are also useful for treating mammals which have undergone or about to undergo, an organ transplant or tissue graft. In tissue transplantation (e.g., kidney, lung, liver, heart) or skin grafting, when there is a mismatch between the class II MHC genotypes (HLA types) of the donor and recipient, there may be a severe "allogeneic immune response" against the donor tissues which results from the presence of non-self or allogeneic class II MHC molecules presenting antigenic peptides on the surface of donor cells.

The activation of lysosomal UCP will inhibit the formation of class II MHC/antigenic peptide complexes, resulting in a suppression or mitigation of tissue rejection. The UCP activator may be used alone or in conjunction with other therapeutic agents, e.g., as an adjunct to cyclosporin A and/or antilymphocyte gammaglobulin to promote graft survival. The administration of the UCP activator with or without other therapeutic agents may be performed before or after the surgery by systemic administration or may be perfused directly into the donor organ or tissue prior to or subsequent to transplantation or grafting.

UCP activators also include UCP peptides which can be delivered to or expressed within a lysosome of a cell such as an APC. APC is used herein to specifically refer to immune cells that can express MHC class II/antigen on the surface. In some cases, this class of compounds includes peptides which are complete UCP proteins or functionally active fragments which are targeted to the lysosome. In other embodiments, this class of compounds includes nucleic acids which produce a lysosomal targeted UCP. Other preferred lysosomal UCP activators are lysosomal targeted omega-3 fatty acids, such as oleic acid, palmitic acid and myrisitate.

In some aspects the methods of the invention include methods for preventing cholesterol trafficking. The method is accomplished by administering a lysosomal UCP activator to a subject to prevent lipid accumulation. Although applicants are not bound by the mechanism it is believed that lysosomal UCP activators prevent cholesterol trafficking by increasing UCP activity and thus promoting use of fatty acids for fuel. Inactive lysosomal UCP results in lipid accumulation leading to cholesterol accumulation.

The lysosomal UCP activators are also useful for preventing inflammatory disease. Inflammatory disease is characterized by inflammation associated with neutrophil accumulation and activation due to excessive neutrophil stimulation. While not intending to be bound by any particular theory, it is believed that when lysosomal UCP is inactive neutrophils undergo respiratory burst and actively accumulate at a site of injury, where they release toxic factors and damage surrounding tissue. When UCP is active in the lysosome neutrophil activation is inhibited and the toxic factors are not released into the surrounding tissues. When the inflammatory disease is an acute stroke a tissue which is often damaged by neutrophil stimulation is the brain. As the active neutrophils accumulate in the brain an infarct may develop.

An "inflammatory disease or condition" as used herein refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil activation. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

The invention also includes compositions of the above described agents. One composition of the invention includes an UCP associated with a plasma membrane targeting molecule. Each of these compounds is described above in more detail. Another composition of the invention includes an UCP inhibitor associated with a plasma membrane targeting molecule.

Each of the compositions of the invention may optionally be associated with a delivery system or vector. In its broadest sense, a "vector" is any vehicle capable of facilitating: (1) delivery of a composition to a target cell or (2) uptake of a composition by a target cell, if uptake is important. Optionally, a "targeting ligand" (in addition to or the same as the plasma membrane targeting molecule) can be attached to the vector to selectively deliver the vector to a cell which expresses on its surface the cognate receptor for the targeting ligand. In this manner, the vector (containing a composition of the invention) can be selectively delivered to a cell in, e.g., a tumor. In general, the vectors useful in the invention are divided into two classes: colloidal dispersion systems and biological vectors.

As used herein, a "colloidal dispersion system" refers to a natural or synthetic molecule, other than those derived from bacteriological or viral sources, capable of delivering to and releasing the composition in a subject. Colloidal dispersion systems include macromolecular complexes, nanocapsules, microspheres, beads, and lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0μ can encapsulate large macromolecules within the aqueous interior and these macromolecules can be delivered to cells in a biologically active form (Fraley, et al., *Trends Biochem. Sci.*, 6:77 (1981)).

Lipid formulations for transfection are commercially available from QIAGEN, for example as EFFECTENE™ (a non-liposomal lipid with a special DNA condensing enhancer) and SUPER-FET™ (a novel acting dendrimeric technology) as well as Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes were described in a review article by Gregoriadis, G., *Trends in Biotechnology* 3:235-241 (1985), which is hereby incorporated by reference.

In one particular embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application serial no. 213,668, filed Mar. 15, 1994). PCT/US/0307 describes a biocompatible, preferably biodegradable polymeric matrix for containing an exogenous gene under the control of an appropriate promotor. The polymeric matrix is used to achieve sustained release of the exogenous gene in the patient. In accordance with the instant invention, the compositions of the invention described herein are encapsulated or dispersed within the biocompatible, preferably biodegradable polymeric matrix disclosed in PCT/US/03307.

The polymeric matrix preferably is in the form of a microparticle such as a microsphere (wherein the composition is dispersed throughout a solid polymeric matrix) or a microcapsule (wherein the composition is stored in the core of a polymeric shell). Other forms of the polymeric matrix for containing the composition include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and composition are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time.

In another embodiment the chemical/physical vector is a biocompatible microsphere that is suitable for oral delivery. Such microspheres are disclosed in Chickering et al., *Biotech. And Bioeng.*, (1996) 52:96-101 and Mathiowitz et al., *Nature*, (1997) 386:410-414.

Both non-biodegradable and biodegradable polymeric matrices can be used to deliver the compositions of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the compositions of the invention are delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

It is envisioned that the UCP or UCP inhibitor may be delivered to the subject in a biological vector which is a nucleic acid molecule which encodes for the UCP or UCP inhibitor such that the UCP or UCP inhibitor must be expressed in vivo. The nucleic acid encoding the UCP or UCP inhibitor is operatively linked to a gene expression sequence which directs the expression of the UCP or UCP inhibitor nucleic acid within a eukaryotic cell. The "gene expression sequence" is any regulatory nucleotide sequence, such as a promoter sequence or promoter-enhancer combination, which facilitates the efficient transcription and translation of the UCP or UCP inhibitor nucleic acid to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined UCP or UCP inhibitor nucleic acid. The gene expression sequences optionally include enhancer sequences or upstream activator sequences as desired.

The UCP or UCP inhibitor nucleic acid is operatively linked to the gene expression sequence. As used herein, the UCP or UCP inhibitor nucleic acid sequence and the gene expression sequence are said to be "operably linked" when they are covalently linked in such a way as to place the expression or transcription and/or translation of the UCP or UCP inhibitor coding sequence under the influence or control of the gene expression sequence. Two DNA sequences are said to be operably linked if induction of a promoter in the 5' gene expression sequence results in the transcription of the UCP or UCP inhibitor sequence and if the nature of the linkage between the two DNA sequences does not (1) result in the introduction of a frame-shift mutation, (2) interfere with the ability of the promoter region to direct the transcription of the UCP or UCP inhibitor sequence, or (3) interfere with the ability of the corresponding RNA transcript to be translated into a protein. Thus, a gene expression sequence would be operably linked to an UCP or UCP inhibitor nucleic acid sequence if the gene expression sequence were capable of effecting transcription of that UCP or UCP inhibitor nucleic acid sequence such that the resulting transcript is translated into the desired protein or polypeptide.

The UCP or UCP inhibitor nucleic acid of the invention may be delivered to the cell alone or in association with a vector. In its broadest sense, a "vector" is any vehicle capable of facilitating the transfer of the UCP or UCP inhibitor nucleic acid to the appropriate cells so that the UCP or UCP inhibitor can be expressed on the plasma membrane or within the cell respectively. Preferably, the vector transports the nucleic acid to the cells with reduced degradation relative to the extent of degradation that would result in the absence of the vector. The vector optionally includes the above-described gene expression sequence to enhance expression of the UCP or UCP inhibitor nucleic acid. In general, the vectors useful in the invention include, but are not limited to, plasmids, phagemids, viruses, other vehicles derived from viral or bacterial sources that have been manipulated by the insertion or incorporation of the UCP or UCP inhibitor nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Clifften, N.J. (1991).

A preferred virus for certain applications is the adeno-associated virus, a double-stranded DNA virus. The adeno-associated virus can be engineered to be replication—deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See e.g., Sambrook et al., "Molecular Cloning: A Laboratory Manual," Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC 19, pRC/CMV, SV40, and pBlueScript. Other plasmids are well-known to those of ordinary skill in the art. Additionally, plasmids may be custom designed using restriction enzymes and ligation reactions to remove and add specific fragments of DNA.

It has recently been discovered that gene carrying plasmids can be delivered to the cells in vivo using bacteria. Modified forms of bacteria such as *Salmonella* can be transfected with the plasmid and used as delivery vehicles. The bacterial delivery vehicles can be administered to a host subject orally or by other administration means. The bacteria deliver the plasmid to cells probably by passing through the gut barrier. High levels of expression have been established using this methodology.

Compaction agents also can be used alone, or in combination with, a vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the compositions in a form that is more efficiently taken up by the cell or, more preferably, in combination with one or more of the above-described vectors.

Other exemplary compositions that can be used to facilitate uptake by a target cell of the compositions of the invention include calcium phosphate and other chemical mediators of intracellular transport, microinjection compositions, electroporation and homologous recombination compositions (e.g., for integrating a composition of the invention into a preselected location within the target cell chromosome).

The pharmaceutical preparations of the invention are administered to subjects in effective amounts. An effective amount means that amount necessary to delay the onset of, inhibit the progression of, halt altogether the onset or progression of or diagnose the particular condition being treated. In one embodiment the compositions are present in an effective dose for treating a tumor. In another embodiment the compositions are present in an effective dose for treating type II diabetes. In general, an effective amount for treating cancer and type I diabetes will be that amount necessary to favorably affect mammalian cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Generally, doses of active compounds will be from about 0.01 mg/kg per day to 1000 mg/kg per day. It is expected that doses range of 50-500 mg/kg will be suitable, in one or several administrations per day. In the event that a response in a subject is insufficient at the initial doses applied, higher doses (or effectively higher doses by a different, more localized delivery route) may be employed to the extent that patient tolerance permits. Multiple doses per day are contemplated to achieve appropriate levels of compounds.

In other aspects the invention includes transgenic animals and cells transfected with the UCP's. Additionally, complements of the UCP nucleic acids described above can be useful as anti-sense oligonucleotides, e.g., by delivering the anti-sense oligonucleotide to an animal to induce a "knockout" phenotype. The administration of anti-sense RNA probes to block gene expression is discussed in Lichtenstein, C., *Nature* 333:801-802 (1988).

Alternatively, the UCP nucleic acids can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of UCP knockout and transgenic animals as models for the study of proliferative disorders.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division. See e.g., Brinster et al., *Proc. Nat. Acad. Sci. USA*, 82: 4438 (1985), Brinster et al., *cell* 27: 223 (1981); Costantini et al., *Nature* 294: 982 (1981); Harpers et al., *Nature* 293: 540 (1981); Wagner et al., *Proc. Nat. Acad. Sci. USA* 78:5016 (1981); Gordon et al., *Proc. Nat. Acad. Sci. USA* 73: 1260 (1976). The fertilized egg is then implanted into the uterus of the recipient female and allowed to develop into an animal.

An alternative method for producing transgenic animals involves the incorporation of the desired gene sequence into a virus which is capable of affecting the cells of a host animal. See e.g., Elbrecht et al., *Molec. Cell. Biol.* 7: 1276 (1987); Lacey et al., *Nature* 322: 609 (1986); Leopol et al., *Cell* 51: 885 (1987). Embryos can be infected with viruses, especially retroviruses, modified to carry the nucleotide sequences which encode UCP proteins or sequences which disrupt the native UCP gene to produce a knockout animal.

Another method for producing transgenic animals involves the injection of pluripotent embryonic stem cells into a blastocyst of a developing embryo. Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. See e.g., Robertson et al., *Cold Spring Harbor Conference Cell Proliferation* 10: 647 (1983); Bradley et al., *Nature* 309: 255 (1984); Wagner et al., *Cold Spring Harbor Symposium Quantitative Biology* 50: 691 (1985).

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia,* 47: 897-905 (1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell,* 63.1099-1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J Robertson, supra).

DNA molecules introduced into ES cells can also be integrated into the chromosome through the process of homologous recombination. Capecchi, *Science,* 244: 1288-1292 (1989). Methods for positive selection of the recombination event (e.g., neo resistance) and dual positive-negative selection (e.g., neo resistance and gangcyclovir resistance) and the subsequent identification of the desired clones by PCR have been described by Capecchi, supra and Joyner et al., *Nature,* 338: 153-156 (1989). The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

Procedures for the production of non-rodent mammals and other animals have been discussed by others. See Houdebine and Chourrout, supra; Pursel et al., *Science* 244: 1281-1288 (1989); and Simms et al., *Bio/Technology* 6: 179-183 (1988).

Inactivation or replacement of the endogenous UCP genes can be achieved by a homologous recombination system using embryonic stem cells. The resultant transgenic non-human mammals having a knockout characteristic may be used as a model for disorders involving abnormally low levels of proliferation. Resistant tumor cells which do not express UCPs may develop as a result of the inability to express UCP on the plasma membrane. A variety of therapeutic drugs can be administered to the phenotypically chemotherapeutic resistant animals to determine the affect of the therapeutic drugs on nerve cell differentiation. In this manner, therapeutic drugs which are useful for preventing or reducing these disorders can be identified.

Additionally, a normal or mutant version of UCP can be inserted into the mouse germ line to produce transgenic animals which constitutively or inducible express the normal or mutant form of UCP in the plasma membrane. These animals are useful in studies to define the role and function of UCP in cells and to observe disorders associated with abnormally high proliferation, such as tumors or autoimmune disease.

The UCP inhibitors and activators described herein are commercially available compounds, are derived from commercially available compounds or are synthesized de novo using routine chemical synthetic procedures known to those of ordinary skill in the art and/or described herein.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. As used herein, the compositions of the invention may include various salts.

The compositions of the invention may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the compositions of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the compositions of the invention into association with a carrier which constitutes one or more accessory ingredients. In general, the compositions are prepared by uniformly and intimately bringing the compositions of the invention into association with a liquid carrier, a finely divided solid carrier, or both, and then, if necessary, shaping the product.

Compositions suitable for oral administration may be presented as discrete units, such as capsules, tablets, lozenges, each containing a predetermined amount of the compositions of the invention. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the compositions of the invention is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The inhibitors and activators of the invention can be administered by any method which allows the inhibitor or activator to reach the target cells, e.g., class II MHC antigen-presenting cells. These methods include, e.g., injection, infusion, deposition, implantation, anal or vaginal supposition, oral ingestion, inhalation, topical administration, or any other method of administration where access to the target cell by the inhibitor is obtained. In some embodiments, topical administration is preferred, due to the high concentration of APCs in the skin. One method for accomplishing topical administration includes transdermal administration, such as iontophoresis. Iontophoretic transmission can be accomplished by using commercially-available patches which deliver a compound continuously through unbroken skin for periods of hours to days to weeks, depending on the particular patch. This method allows for the controlled delivery of the inhibitors or activators through the skin in relatively high concentrations. One example of an iontophoretic patch is the LECTRO PATCH™ sold by General Medical Company of Los Angeles, Calif. The patch provides dosages of different concentrations which can be continuously or periodically administered across the skin using electronic stimulation of reservoirs containing the inhibitors or activators. Topical administration also includes epidermal administration which involves the mechanical or chemical irritation of the outermost layer of the epidermis sufficiently to provoke an immune response to the irritant. The irritant attracts APCs to the site of irritation where they can then take up the inhibitor or activator. One example of a mechanical irritant is a tyne-containing device. Such a device contains tynes which irritate the skin and deliver the drug at the same time. For instance, the MONO VACC manufactured by Pasteur Merieux of Lyon, France. The device contains a syringe plunger at one end and a tyne disk at the other. The tyne disk supports several narrow diameter tynes which are capable of scratching the outermost layer of epidermal cells. Chemical irritants include, for instance, keratinolytic agents, such as salicylic acid and can be used alone or in conjunction with mechanical irritants.

Injections can be e.g., intravenous, intradermal, subcutaneous, intramuscular, or interperitoneal. For example, the inhibitor can be injected intravenously or intramuscularly for the treatment of multiple sclerosis, or can be injected directly into the joints for treatment of arthritic disease, or can be injected directly into the lesions for treatment of pemphigus vulgaris. The activator can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the inhibitor or activator with an aerosol in an inhaler, either alone or attached to a carrier that can be absorbed. For systemic administration, it may be preferred that the inhibitor or activator is encapsulated in liposomes.

In certain embodiments of the invention, the administration can be designed so as to result in sequential exposure of the inhibitor or activator over some period of time, e.g., hours, days, weeks, months or years. This can be accomplished by repeated administrations of the inhibitor or activator, by one of the methods described above, or alternatively, by a controlled-release delivery system in which the inhibitor or activator is delivered to the mammal for a prolonged period without repeated administrations. By controlled-release delivery system, it is meant that total release of the inhibitor or activator does not occur immediately upon administration, but rather is delayed for some period of time. Release can occur in bursts or it can occur gradually and continuously. Administration of such a system can be, e.g., by long-lasting oral dosage forms, bolus injections, transdermal patches, and subcutaneous implants.

Examples of systems in which release occurs in bursts includes, e.g., systems in which the inhibitor or activator is entrapped in liposomes which are encapsulated in a polymer matrix, the liposomes being sensitive to specific stimuli, e.g., temperature, pH, light or a degrading enzyme and systems in which the inhibitor or activator is encapsulated by an ionically-coated microcapsule with a microcapsule core degrading enzyme. Examples of systems in which release of the inhibitor is gradual and continuous include, e.g., erosional systems in which the inhibitor or activator is contained in a form within a matrix and effusional systems in which the inhibitor or activator permeates at a controlled rate, e.g., through a polymer. Such sustained release systems can be e.g., in the form of pellets, or capsules.

The inhibitor or activator can be suspended in a liquid, e.g., in dissolved form or colloidal form. The liquid can be a solvent, partial solvent, or non-solvent. In many cases, water or an organic liquid can be used.

The inhibitor and activator are administered to the mammal in a therapeutically-effective amount. The therapeutically-effective amount is meant that amount which is capable of at least partially preventing, reversing, reducing, decreasing, ameliorating, or otherwise suppressing the particular immune response being treated, when an inhibitor is administered or inducing, activating, or otherwise increasing a particular immune response when an activator is administered. A therapeutically-effective amount can be determined on an individual basis and will be based, at least in part, on consideration of the species of mammal, the mammal's age, sex, size, and health; the inhibitor or activator used, the type of delivery system used; the time of administration relative to the severity of the disease; and whether a single, multiple, or controlled-release dose regiment is employed. A therapeutically-effective amount can be determined by one of ordinary skill in the art employing such factors and using no more than routine experimentation.

In some embodiments, the concentration of the inhibitor or activator if administered systemically is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. Preferably, the concentration of the inhibitor or activator, if applied topically, is about 0.1 mg to about 500 mg/gm of ointment or other base, more preferably about 1.0 mg to about 100 mg/gm of base, and most preferably, about 30 mg to about 70 mg/gm of base. The specific concentration partially depends upon the particular inhibitor or activator used, as some are more effective than others. The dosage concentration of the inhibitor or activator actually administered is dependent at least in part upon the particular immune response being treated, the final concentration of inhibitor or activator that is desired at the site of action, the method of administration, the efficacy of the particular inhibitor or activator, the longevity of the particular inhibitor or activator, and the timing of administration relative to the severity of the disease. Preferably, the dosage form is such that it does not substantially deleteriously effect the mammal. The dosage can be determined by one of ordinary skill in the art employing such factors and using no more than routine experimentation.

The lysosomal UCP inhibitors of the invention can be administered in combination with other therapeutics. For instance the inhibitors can be administered in combination with anti-infective agents. Antibiotics which are effective in treating a wide variety of diseases in humans and animals including tuberculosis (caused by *Mycobacterium tuberculosis, Mycobacterium bovis*, and other *Mycobacteria*), leprosy, *Mycobacterium avium* complex (MAC) infections, *Mycobacterium marinum* infection, *Mycobacterium fortuitum* infection, *Mycobacterium Kansaii* infection, brucellosis, Q fever, tularemia, salmonellosis, typhoid fever, *Yersinia* infections (including *Y. pestis, Y. enterocolitica* and *Y. pseudotuberculosis*), ehrlichiosis, chlamydiosis (including *C. psittaci, C. trachomatis*), histoplasmosis, toxoplasmosis and leishmaniasis, include but are not limited to rifampin, rifabutin, isoniazid, ethambutol, pyrazinamide, thiacetazone, para-aminosalicylic acid, aminoglycosides (including gentamycin, streptomycin, amikacin, kanamycin, viomycin, capreomycin, quinolones (including ciprofloxacin, ofloxacin), ethionamide, prothionamide, cycloserine, dapsone, clofazimine, sparfloxacin, minocycline, clarithromycin, azithromycin, doxycycline, cefoxitin, tetracyclines, cefotaxime, fluoroquinolones, ceftriaxone, chloramphenicol, trimethaprim-sulfamethoxazole, ampicillin, sulfonamides, amoxicillin, ketoconazole, itraconazole, fluconazole, pyrimethamine sulfadiazine, clindamycin, atovaquone sodium stibogluconate, antimonials, amphotericin B, pentamidine, polymixin definsins and other peptide antibiotics used to treat intracellular pathogens. Preferred antibiotics are those which are designed to treat diseases that are caused by intracellular pathogens.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Example 1

Metabolic State of a Cell is Indicative of Cell Surface Fas Expression and Sensitivity/Resistance to Cell Death 1. Resistance to apoptosis is characterized by failure to express Fas: The cell lines utilized herein include L1210, a leukemic cell line; HL60, a human pro-myelocytic cell line; and PC12, a pheochromocytoma cell line which can be induced to differentiate into a neuronal cell line in the presence of NGF (Lindenboim, L, et al., *Cancer Res*, 1995, 55:1242-7). Each cell line was examined in parallel with apoptotic resistant sublines: L1210 DDP, HL60 MDR, and PC 12Trk. L 1210 DDP are resistant to cisplatin and methotrexate; HL60 MDR are resistant to adriamycin induced apoptosis; PC12 TrkA, which have been transfected with TrkA which results in constitutively expression the NGF receptors, are not susceptible to alcohol and NGF withdrawal as are the PC 12 cells.

The apoptosis sensitive cells from each tissue origin were morphologically round, non-adherent, rapidly dividing cells, with the exception of the PC 12 cell line. The apoptosis resistant cells from all tissue origins were morphologically large, adherent, and slowly dividing cells.

The recently characterized molecules, Fas (CD95) and Fas Ligand (CD95L), have been strongly implicated in the process of apoptotic death (Muller, M, et al., *J. Clin Invest*, 1997, 99:403-413). We examined expression of Fas on the above-identified cell lines. Flow cytometric analysis of Fas expression was performed using an isotype versus FITC-anti-Fas (Pharmingen) on L1210; PC12; and HL60 cells and resistant cell lines L1210DDP, PC12Trk; and HL60MDR. A Coulter Epics Elite flow cytometer with a single excitation wavelength (488 nm) and band filters for PE (575 nm), FITC (525 nm) and Red613 (613 nm) was used to analyze the stained cells. Each sample population was classified for cell size (forward scatter) and complexity (side scatter), gated on a population of interest and evaluated using 40,000 cells. Criteria for positive staining were established by comparison with the intensity of the isotype controls, thick lines. Independent of tissue origin, all of the apoptosis resistant lines fail to express cell surface Fas both constitutively and in the presence of agents that induce apoptosis in the parental cell lines.

2. Resistance to apoptosis is characterized by relatively high rates of glucose oxidation and utilization: We performed experiments to examine the correlation between cell surface Fas expression and glucose metabolism. As a prototype for the Fas positive and Fas negative cells we used the L1210 and the L1210DDP cell lines, as Fas positive and Fas negative, respectively. We directly measured the rates of glucose utilization and oxidation of L1210 and L1210DDP. Ratios were generated by using nanomolar values.

Rate of glucose utilization was measured by the method of Ashcroft et al. Briefly, cells were incubated 90 min at 37° C. in 100 µl KRB, glucose (5.5 mM), 1.3 µCi D-[5-$^3$H] glucose (Amersham, Arlington Heights, Ill.). The reaction was carried out in a 1 ml cup contained in a rubber stoppered 20 ml scintillation vial that had 500 µl of distilled water surrounding the cup. Glucose metabolism was stopped by injecting 100 µl 1 M Hcl through the stopper into the cup. An overnight incubation at 37° C. was carried out to allow equilibration of the [$^3$H]-$H_2O$ in the reaction cup and the distilled water, followed by liquid scintillation counting of the distilled water.

Rate of glucose oxidation was measured by incubating cells for 90 min at 37° C. in 100 ml of reaction buffer, glucose (2.8, 8.3, 27.7 mmol/l), 1.7 mCi (U-14C glucose). The reaction was carried out in a 1 ml cup in a 20 ml scintillation vial capped by a rubber stopper with a center well that contains filter paper. Metabolism was stopped and $CO_2$ liberated with 300 ml 1 mol/l HCl injected through the stopper into the cup containing the cells. $CO_2$ was trapped in the filter paper by injecting 10 ml 1 mol/l KOH into the center well, followed 2 hours later by liquid scintillation counting. Tubes containing $NaHCO_3$ and no cells were used to estimate the recovery of $^{14}CO_2$ in the filter paper, routinely close to 100%.

The results are presented in Table 1.

TABLE 1

| Glucose Metabolism in L1210/0 and L1210/DDP | | |
|---|---|---|
| | L1210/0 | L1210/DDP |
| Glucose Utilization (pmol glucose/90 min/50,000 cells) | 1740 ± 920 | 3470 ± 460 |
| Glucose Oxidation (pmol glucose/90 min/50,000 cells) | 235 ± 7 | 428 ± 124 |
| Glucose Utilization/Oxidation | 7.4 | 8.1 |

Because the L1210 and L1210DDP cells are tumor cell lines and are likely to have increased ratios of glucose oxidation to utilization (Warburg, O., et al., *Klin Woch*, 1926, 5:829-832), we measured glucose utilization on normal lymphocytes. We isolated $10^6$ splenic lymphocytes from C57BL/6 animals, Fas-deficient C57BL/6 (B6.1pr), and FasL defective C57BL/6 (B6.gld) animals. The rate of glucose utilization and oxidation of the Fas deficient and the FasL deficient lymphocytes are demonstrated in Table 2. The ratio of glucose utilization to oxidation is highest in lpr lymphocytes and lowest in wild type normal, quiescent lymphocytes.

TABLE 2

Glucose Metabolism in Lymphocytes from Normal, Fas Deficient and FasL Deficient Mice

|  | b6 | lpr | gld |
|---|---|---|---|
| GLUCOSE UTILIZATION |  |  |  |
| (nmol glucose/90 mins/50,000 cells) | 0.04 | 0.36 | 0.22 |
| GLUCOSE OXIDATION |  |  |  |
| (pmol glucose/90 mins/50,000 cells) | 73.24 | 164.51 | 122.82 |

|  | CELL TYPE | RATIO |
|---|---|---|
| GLUCOSE UTILIZATION/ GLUCOSE OXIDATION | b6 | 0.55 |
|  | lpr | 2.19 |
|  | gld | 1.79 |

These data (Table 1 & 2) demonstrate high rates of glucose utilization and oxidation of both tumor lines relative to the normal lymphocytes; and higher rates of glucose utilization and oxidation of the apoptotic resistant line relative to the wild type. There is an important difference in the ratio of glucose utilization to oxidation between normal and Fas or FasL deficient animals, with the ratio being higher for lymphocytes from both mutant strains of animals. The consequences of uncoupling are a decrease in mitochondrial membrane potential; use of fat as a carbon source increased rate of glycolysis, increased rate of electron transport, and energy dissipation, in a form other than ATP. These data suggest that there is an increase in proton leak in the cells with high rates of glucose oxidation and utilization relative to the normal cells, suggesting some degree of uncoupling may have occurred in these cells.

3. Fas Expression Increases as a Function of Glucose: We investigated the effect of increasing concentrations of glucose on cell surface Fas expression. L1210 and L1210/DDP cells were cultured in glucose free RPMI media or in media supplemented with insulin and glucose for 16 hours. Intra- and extracellular Fas expression was determined by labeling the cells with FITC-conjugated anti-Fas antibodies (Pharmingen), or FITC-conjugated isotype control, then subtracting the fluorescence intensity of the isotype staining from Fas staining for each treatment group.

These data showed that Fas expression increases as a function of glucose concentration and that as a result the cell surface Fas negative L1210/DDP begin to express cell surface Fas.

4. Treatment of L1210 DDP cells with staurosporin restores Fas expression and susceptibility to drug-induced apoptosis: L1210, but not L1210 DDP, undergo apoptotic cell death. We treated L1210 or L1210 DDP cells with the staurosporin, which inhibits protein kinase C and increases mitochondrial membrane potential, or an anti-cancer agent to which both cells are sensitive, adriamycin. Fas expression was increased or induced on both L1210 and L1210 DDP, respectively, in the presence of staurosporin or adriamycin. The L1210 DDP changed morphologically and began to divide rapidly, changes which appeared to correspond with a reversion back to the phenotype of the L1210 cells. These results demonstrate that Fas expression results in parallel with altered metabolic activity.

5. Confocal microscopy reveals that resistance to apoptosis is characterized by intra-(but not extra) cellular Fas expression: L1210 DDP cells express no cell surface Fas. To address the possibility that Fas is expressed, but has been targeted to a subcellular organelle, we permeabilized and stained L1210 and L1210DDP cells with fluorochrome conjugated anti-Fas antibody (J02.2, Pharmingen). The cells were examined by confocal microscopy. (This experiment was representative of four experiments).

Our data indicate that L1210 DDP cells express Fas in an intracellular, cytosolic compartment. Fluorochrome-conjugated isotype matched antibody was used as control. Additionally, these data also demonstrate that the Fas negative, apoptosis resistant cells, express intracellular Fas.

6. Fas-deficient (lpr) lymphocytes express intra-(but not extra-) cellular Fas molecules: We isolated lymphocytes from spleens of C57BL/6 mice and from C57BL6 transgenics having the lpr mutation (loss of Fas sensitivity). Cells were stained with fluorescein conjugated hamster anti-Fas and examined by confocal microscopy.

Results demonstrate that unstimulated, non-permeabilized splenocytes from C57BL/6 animals express Fas at low levels relative to isotype controls. Interestingly, significant levels of Fas expression were detected in permeabilized normal lymphocytes. As expected, non-permeabilized cells from C57BL6.1pr animals express no detectable cell surface Fas relative to isotype control. Interestingly, intracellular Fas staining of permeabilized splenocytes from C57Bl/6.lpr animals reveals intracellular expression of Fas. These results demonstrate that mutations affecting susceptibility to Fas-induced death prevent cell surface, but not intracellular expression of the Fas molecule.

7. Anti-cancer agents induce susceptibility to Fas-induced cell death: To determine if the anti-cancer agent methotrexate sensitizes L1210 or L1210/DDP cells to Fas induced cell death, we cultured L1210 cells in the presence or absence of $10^{-8}$ M methotrexate for 72 hours. Each group of cells was cultured on uncoated plates or plates coated with 10 g/ml anti-Fas (Jo.2.2, Pharmingen). We analyzed cell death using flow cytometry. Forward angle and 90 degree light scatter were used to distinguish between live and dead cells. Dead cells were gated as forward angle light scatter low/high ethidium bromide retaining cells. Percent death was calculated over the total number of cells acquired. In Table 3 below, values indicate % dead cells over background of untreated cells.

TABLE 3

| Fas-induced cell death | | |
|---|---|---|
|  | L1210/0 | L1210/DDP |
| Control | 4.72 | 40.88 |
| anti-Fas Coated Plates | 79.98 | 46.60 |

Additionally, L1210 and L1210/DDP cells were treated with 10-8 M methotrexate for 24 hours. Flow cytometric analysis revealed two populations based on forward side scatter. The forward scatter high populations did not take ethidium bromide and were therefore viable. The forward scatter low populations took up ethidium bromide differentially. The L1210 cells took up a moderate amount. Analysis of DNA fragments reveals that L1210 produced a ladder of nucleosome sized fragments indicative of apoptosis, whereas L1210/DDP cells did not. This latter phenotype—loss in forward scatter and membrane permeability with no "DNA laddering"—is the hall mark of oncosis.

8. Fas Deficient Lymphocytes are also drug resistant to methotrexate: We isolated splenic lymphocytes from aged-matched wild type C57BL/6 mice and C57BL6.1pr and C57BL.gld. Splenocytes from C57BL/6 lpr or gld animals were isolated, red cells depleted, and single cell suspensions prepared. Cells were cultured in the absence or presence of $5 \times 10^{-8}$ M methotrexate for 18 or 32 hours. Cells were harvested and viability was determined by flow cytometric analysis and confirmed with trypan blue exclusion.

The data demonstrate decreased susceptibility to methotrexate-induced apoptosis in Fas deficient lymphocytes. These data are consistent with the notion that Fas is required for drug susceptibility.

9. Drug resistant cells express intracellular fas, UCP and bcl-2: We determined if wild type and/or drug resistant cells express intracellular and surface fas, UCP and bcl-2. We stained non-permeabilized L1210 and L1210/DDP cells for cell surface or intracellular Fas. The data show that while there is no cell surface expression of Fas on the drug/apoptotic resistant cells, the drug resistant cells express high levels of intracellular Fas. The drug resistant cells are cell surface Fas negative and protected from death resulting from changes in mitochondrial membrane permeability transitions.

10. Cell surface and Intracellular Fas levels in Melanoma Cells.

B16 cells were cultured in the in the presence of different concentrations of sodium acetate and Fas expression was measured. The data showed the level of cell surface Fas expression on non-permeabilized and intracellular Fas expression in permeabilized B16 melanoma cells. With increasing concentrations of sodium acetate, the levels of intracellular Fas declined and the levels of cell surface Fas increased, demonstrating a translocation of Fas from intracellular stores to the surface.

The rates of glucose utilization and oxidation in B16 melanoma cells also was determined. Again cells were cultured in the presence of varying concentration of sodium acetate. Both glucose utilization and glucose oxidation (measured in nmoles) decreased with increasing concentrations of sodium acetate, demonstrating a correlation with expression of cell surface Fas in the same cells.

11. Sodium Acetate increases cell surface Fas expression.

Sodium Acetate as a mitochondrial modifying agent was examined. L1210 or L1210DDP cells were cultured in the presence of graded concentrations of sodium acetate in the medium. Cells were stained with Jo2.2, a fluorescein conjugated anti-Fas antibody, or an isotype control. Cell surface staining was measured flow cytometrically. The percentage of mean fluorescence intensity over the isotype control was plotted. The data indicate that the presence of acetate increases cell surface Fas expression in both cell lines.

The effects of acetate on susceptibility to Fas-dependent cell death were also examined. Cells cultured with acetate were loaded with 51 Cr and plated onto FasLbearing or mock transfected fibroblast to determine sensitivity to Fas-induced cell death. The data indicate that in a dose dependent manner, culture of both cell types with acetate resulted in susceptibility to Fas-dependent cell death.

Example 2

Metabolic State of a Cell is Indicative of Cell Surface and Intracellular UCP Expression and Sensitivity/Resistance to Cell Death 1. Intracellular UCP is Present in a Panel of Tumor Cells.

We extended our analysis of intracellular expression of UCP to other tumor cells. Intracellular UCP expression was examined flow cytometrically on cells which had been permeabilized and stained as indicated. The histograms represent FITC isotype control versus stained with Rabbit anti-UCP (a kind gift of Mary Ellen Harper) FITC-anti-Rabbit. A Coulter Epics Elite flow cytometer with a single excitation wavelength (488 nm) and band filters for PE (575 nm), FITC (525 nm) and Red613 (613 nm) was used to analyze the stained cells. Each sample population was classified for cell size (forward scatter) and complexity (side scatter), gated on a population of interest and evaluated using 40,000 cells. Criteria for positive staining were established by comparison with isotype controls, thin lines to specific stain, thick lines.

All of the tumor cells lines examined express UCP intracellularly. These data are consistent with the idea that expression of UCP in tumor cells is generalizable to all tumor cells, and likely results from the well documented shift in subcellular production of ATP from mitochondria to cytosol as cells divide. Importantly, these data also demonstrate that expression of UCP2 is not specific to lymphoid tumors. The L929 cells are fibroblasts and the PC 12 Trk cells which are derived from pheochromocytoma cell lines, respectively. The EL4 cells are a mouse thymoma cell line and Jurkat are human T cell tumor cells.

To confirm that flow cytometrically detected UCP expression was mitochondrial, we isolated mitochondria from L1210 and L1210 DDP, and performed Western Blot analysis blotting with rabbit anti-UCP antibodies. Mitochondria were isolated using differential centrifugation as adapted from (Reinhart, P H, Taylor, W M and Bygrave F L (1982) A procedure for the rapid preparation of mitochondria from rat liver. *Biochem. J.* 204: 731-735. and Sims NR (1990) Rapid isolation of metabolically active mitochondria from rat brain and subregions using Percoll density gradient centrifugation. *J. Neurochem.* 55:698-707.) The following samples were run: molecular weight markers (BIORAD Biotinylated SDS-PAGE standards; L1210/0 mitochondrial protein (40:g) from two distinct mitochondrial preparations; L1210/DDP mitochondrial protein (40:g) from two distinct mitochondrial preparations; and UCP standard (0.75:g) from rat brown adipose tissue (which expresses UCPs 1-3). Rabbit anti-hamster UCP was used at a dilution of 16,000. The secondary antibody: goat anti-rabbit IgG conjugated to HRP at 1:10,000. Chemiluminescent detection: Amersham ECL kit.

The blot showed greater levels of mitochondrial UCP in the drug resistant L1210/DDP than in L1210/0. The detected mitochondria protein has an approximate molecular weight of 30 kDa, close to the predicted molecular weight of UCP2 (33 kDa).

To determine whether increased UCP corresponded to increased mitochondrial proton leak and a lower mitochondrial membrane potential ($\Delta\psi$m) we assessed characteristics of non-phosphorylating respiration in intact L1210 wild type and L1210 DDP cells. State 4 $\Delta\psi$m in DDP cells, x mV, was significantly lower than in wild type cells, y mV ($p<0.001$), and state 4 oxygen consumption in DDP cells is significantly higher than in wild type cells, indicating increased mitochondrial proton leak.

2. Cell Surface UCP is Present in a Panel of Tumor Cells.

The cell lines utilized herein include L1210, a leukemic cell line; and HL60, a human pro-myelocytic cell line. Each cell line was examined in parallel with apoptotic resistant sublines: L1210 DDP, and HL60 MDR. L1210 DDP are resistant to cisplatin and methotrexate and HL60 MDR are resistant to adriamycin induced apoptosis. The apoptosis sensitive cells from each tissue origin were morphologically round, non-adherent, rapidly dividing cells. The apoptosis resistant cells from all tissue origins were morphologically large, adherent, and slowly dividing cells.

We examined expression of UCP on the plasma membrane of the above-identified cell lines to determine if wild type and/or drug resistant cells express intracellular and surface UCP. We stained non-permeabilized L1210 and L1210/DDP cells for cell surface or intracellular UCP. Flow cytometric analysis of UCP expression was performed using an isotype versus FITC-anti-UCP (described above) on L1210 and HL60 cells and resistant cell lines L1210DDP and HL60MDR. A Coulter Epics Elite flow cytometer with a single excitation wavelength (488 nm) and band filters for PE (575 nm), FITC (525 nm) and Red613 (613 nm) was used to analyze the stained cells. Each sample population was classified for cell size (forward scatter) and complexity (side scatter), gated on a population of interest and evaluated using 40,000 cells. Criteria for positive staining were established by comparison with the intensity of the isotype controls, thick lines.

The apoptosis resistant lines failed to express cell surface UCP (HL60MDR) or expressed lower levels of UCP than the wild type cells (L1210DDP). Each of the wild type cell lines expressed high levels of cell surface UCP. The data demonstrate a correlation between fas and UCP expression. The data described above demonstrate that while there is no cell surface expression of Fas on the drug/apoptotic resistant cells, the drug resistant cells express high levels of intracellular Fas, similar to UCP. The drug resistant cells are cell surface Fas negative and protected from death resulting from changes in mitochondrial membrane permeability transitions.

3. Cell Surface and Intracellular UCP and Fas Levels in Melanoma Cells.

B16 cells were cultured and either permeabilized or unpermeabilized and UCP expression was measured. The data showed the absence of cell surface UCP expression on non-permeabilized B16 cells, similar to drug resistant tumor cells described above. Intracellular UCP expression in permeabilized B16 melanoma cells, on the other hand, was very high.

B16 cells also were cultured in the presence of different concentrations of sodium acetate and Fas expression was measured. The data showed the level of cell surface Fas expression on non-permeabilized and intracellular Fas expression in permeabilized B16 melanoma cells. With increasing concentrations of sodium acetate, the levels of intracellular Fas declined and the levels of cell surface Fas increased, demonstrating a translocation of Fas from intracellular stores to the surface.

The rates of glucose utilization and oxidation in B16 melanoma cells also was determined. Again cells were cultured in the presence of varying concentration of sodium acetate. Both glucose utilization and glucose oxidation (measured in nmoles) decreased with increasing concentrations of sodium acetate, demonstrating a correlation with expression of cell surface Fas in the same cells.

4. UCP-2 mRNA Levels in Tumor Cells.

mRNA was isolated from L1210 wild type cells, L1210-DDP cells, a positive control (brown adipose fat tissue from a UCP-1 negative (−/−) mouse), and a negative control (brown adipose fat tissue from a UCP-1 positive/negative (+/−) mouse) and processed by Northern blot analysis. L1210 wild type cells expressed the highest amounts of UCP-2 mRNA, even higher than positive control cells. L1210-DDP cells expressed much lower levels of UCP-2 than wild type or the positive control cells.

5. UCP Protein Levels in Tumor Cells.

Protein was isolated from plasma membrane of L1210 wild type cells and L1210-DDP cells and processed by Western blot analysis. L1210 wild type cells expressed the highest amounts of plasma membrane UCP. L1210-DDP cells expressed much lower levels of plasma membrane UCP than wild type.

Example 3

Exposure of Chemotherapy Sensitive Tumor Cells but not Chemotherapy Resistant Cells to anti-UCP Antibody Causes Increased Cell Death Chemotherapy-sensitive cells HL60 and chemotherapy resistant cells HL60-MDR were exposed to a labeled anti-UCP antibody (described above) for two 15 minute intervals and subjected to flow cytometry, as described above.

Scatter plots were generated for each sample. In the first plot the forward versus side scatter of untreated HL60 cells represents a population of healthy living cells. When HL60s were treated with the anti-UCP antibody, the forward scatter decreased and the side scatter increased demonstrating a higher number of dead cells present in the population. It is expected that longer incubation times with the anti-UCP antibody will result in a greater number of dead cells within the population. There was no difference between the anti-UCP untreated and treated HL60-MDR cells. The lack of effect of the UCP antibody on HL60MDR cells was expected, since these cells do not express cell surface UCP.

Example 4

Pancreatic B Cells Express Mitochondrial UCP and Have No Cell Surface Fas

1. Loss of antigen in β-cell tumors: Proliferation with two responder T cell clones, BDC-2.5 and BDC-6.9, was tested using NOD peritoneal cells as APC and as antigen, either freshly prepared NOD islet cells (control) or β tumor cells, or NIT-1, an established beta tumor cell line from the NOD-RIPTag mouse. Upon harvesting the islet tumors, the β-cells obtained are fully as antigenic as normal NOD islet cells. The NIT-1 line is also antigenic for these T cell clones, but only at low passage numbers; with continued culture, the line changes its morphology and growth kinetics and undergoes complete loss of antigen.

2. Response of pancreatic β-cells to glucose: The experiments described below were designed to test the hypothesis that β cell metabolism may be linked to immune recognition and destruction. Glucose utilization was measured as [$^3$H] $H_2O$ production from 5-[$^3$H]glucose in normal rat islets. Glucose oxidation was measured as [$^{14}$C]$CO_2$ production from U-[$^{14}$C]glucose. The data show increasing glucose utilization and oxidation in β-cells as a function of increasing glucose concentration.

3. Normal β-cells Express Intracellular UCP2 and No Cell Surface Fas: Normal β-cells have a specialized glucose response which is based on the cell being responsive to physiologic glucose concentrations. The process that mediates the glucose responsiveness is the process involving flux through glycolysis. β-cell glucose usage is mediated through a relatively unique system that entails specialized high $K_m$ glucose transporter (GLUT2) and glucose phosphorylation isoforms (glucokinase). We isolated β-cells from C3H mice, stained the isolated cells with anti-Fas, and electronically gated viable cells. In parallel, cells were permeabilized and stained with an antibody to UCP2 (kindly provided by Drs. Jean Himms-Hagen and M. E. Harper). The data indicated that normal β-cells expressed intracellular UCP2 and no cell surface Fas.

4. Fas Expression and Mitochondrial Membrane Potential are a Function of Glucose Concentration in Mouse β Cells.

The central question is whether Fas expression is altered by changes in physiological glucose concentrations in normal β cells and does the mitochondrial membrane potential increase, suggesting that the cell has ATP synthesis resulting from increased rates of electron transport. Islets were isolated and dispersed with trypsin and a cell strainer. Debris and dead cells were removed and applying the cells to a 1.066 Percoll gradient. Electronic gating of the cells was used to segregate the populations of islets cells. The region with larger cells were gated β cells where the region with smaller cells were gated as alpha cells. Other larger cells were excluded because they contained δ cells. The cells were treated overnight with either physiological 11.1 mM glucose or high glucose 55.5 mM glucose. Fas expression was determined by staining with a FITC conjugated antibody. Mean fluorescence of staining with isotype control antibody was subtracted. Measurement of mitochondrial membrane potential was measured using JC-1 as a fluorescence probe. The relative membrane potential was read by taking the red mean fluorescence (aggregated JC-1 labeled) divided by mean green fluorescent (monomeric JC-1) labeled fluorescence. Our data suggest that as glucose concentration increases, the large β cell subset of gated cells have increased Fas expression and concomitant increased mitochondrial membrane potential, while the smaller (possibly alpha, glucagon producing cells) do not.

5. Determination of Mitochondrial Membrane Potential in β Cells Isolated from Four Strains of Animals.

Mitochondrial membrane potential is assessed flow cytometrically using mitotracker red. The amount of membrane potential was measured in the four strains of animals AB-, AB-Ea, C57Bl/6, BITgEa, described in more detail below. Mitochondrial membrane potential was highest in the AB-strain, followed by the AB-EA stain. The C57Bl/6 and BIT-gEa strains had much lower mitochondrial membrane potential.

Example 5

Overexpression of UCP2 Shifts UCP from Plasma Membrane and Growth Arrests Cells

Overexpression of UCP in L1210 and U937 cells induced a shift to intracellular UCP and caused a phenotypic change to the cells. These cells became growth arrested and chemotherapy resistant. UCP2 also prevented free radical production, thus preventing respiratory burst. Cells transfected with a mock vector remained cell surface UCP positive, chemotherapy sensitive and demonstrated no change with respect to reactive oxygen production.

Example 6

UCP is Expressed in Lysosomal Membranes

UCP stained cells were subjected to confocal microscopy and examined for UCP localization. Surprisingly, UCP was observed in lysosomes of rapidly dividing, drug sensitive cells.

Example 7

Inhibition of Lysosomal Translocation

Tunicamycin was used to demonstrate an inhibition of lysosomal UCP translocation. MDR cells, which are plasma membrane UCP negative and lysosomal UCP positive were treated with tunicamycin. Treatment with the drug caused a shift in the intracellular UCP from the lysosome and mitochondria to the plasma membrane. These same cells were treated with tunicamycin and an-anti-UCP2 antibody. This combination therapy induced cell death, as a result of the expression of UCP on the plasma membrane.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

I claim:

1. A method for inducing cell death in a tumor cell expressing a plasma membrane UCP, comprising:
   contacting the tumor cell with an anti-UCP antibody.

2. The method of claim 1, wherein the tumor cell is in a subject and wherein the plasma membrane targeted UCP inhibitor is administered in vivo.

3. The method of claim 1, wherein the tumor cell is in a subject and wherein the plasma membrane targeted UCP inhibitor is administered ex vivo.

4. The method of claim 1, further comprising the step of administering to the subject a cytotoxic anti-tumor therapy.

* * * * *